(12) United States Patent
Snell

(10) Patent No.: US 10,118,167 B2
(45) Date of Patent: Nov. 6, 2018

(54) METHODS FOR REGENERATING SULFUR-CONTAMINATED AROMATIZATION CATALYSTS

(71) Applicant: Chevron Phillips Chemical Company LP, The Woodlands, TX (US)

(72) Inventor: Ryan W. Snell, Kingwood, TX (US)

(73) Assignee: Chevron Phillips Chemical Company LP, The Woodlands, TX (US)

(*) Notice: Subject to any disclaimer, the term of this patent is extended or adjusted under 35 U.S.C. 154(b) by 0 days.

(21) Appl. No.: 15/384,353

(22) Filed: Dec. 20, 2016

(65) Prior Publication Data
US 2018/0169640 A1   Jun. 21, 2018

(51) Int. Cl.
*B01J 38/10* (2006.01)
*B01J 38/42* (2006.01)
(Continued)

(52) U.S. Cl.
CPC ............ *B01J 29/90* (2013.01); *B01J 29/62* (2013.01); *B01J 37/0018* (2013.01); *B01J 37/0201* (2013.01); *B01J 37/0207* (2013.01); *B01J 37/06* (2013.01); *B01J 37/08* (2013.01); *B01J 37/24* (2013.01); *B01J 37/26* (2013.01); *B01J 37/30* (2013.01); *B01J 38/02* (2013.01); *B01J 38/12* (2013.01); *B01J 38/14* (2013.01); *B01J 38/48* (2013.01); *B01J 38/54* (2013.01); *B01J 38/64* (2013.01); *C07C 5/325* (2013.01); *C07C 5/417* (2013.01); *C10G 35/095* (2013.01); *C10G 45/70* (2013.01); *B01J 2229/42* (2013.01); *B01J 2229/64* (2013.01); *C07C 2529/62* (2013.01);
(Continued)

(58) Field of Classification Search
CPC ... B01J 29/90; B01J 29/62; B01J 38/02; B01J 38/10; B01J 38/12; B01J 38/42; B01J 38/46; B01J 38/48; B01J 38/64; B01J 27/045; B01J 27/10; B01J 27/12; B01J 27/13; C07C 5/417; C07C 2529/62
USPC ......... 502/20, 22, 25, 32, 66, 218, 223, 230, 502/327, 330, 334, 339; 208/140
See application file for complete search history.

(56) References Cited

U.S. PATENT DOCUMENTS 2,344,208 A * 3/1944 Kirkpatrick .............. B01J 23/96
                                                                   252/DIG. 18
2,381,659 A * 8/1945 Frey ........................ B01J 23/94
                                                                   502/25

(Continued)

FOREIGN PATENT DOCUMENTS

| EP | 0 201 856 B1 | 1/1991 |
| EP | 2 170 509 B1 | 8/2015 |
| WO | WO 86/02861 | 5/1986 |

OTHER PUBLICATIONS

Fukunaga et al., entitled "The Nature of the High Sensitivity of Pt/KL Catalysts to Sulfur Poisoning," Journal of Catalysis, 1995, vol. 157, pp. 550-558.

(Continued)

*Primary Examiner* — Patricia L. Hailey
(74) *Attorney, Agent, or Firm* — Merchant & Gould P.C.

(57) ABSTRACT

Methods for regenerating a sulfur-contaminated catalyst are disclosed. Such methods may employ a step of washing the sulfur-contaminated catalyst with an aqueous solution containing an alkali metal, followed by contacting the washed catalyst with a halogen solution containing chlorine and fluorine.

40 Claims, 8 Drawing Sheets

(51) Int. Cl.
| | |
|---|---|
| *B01J 38/46* | (2006.01) |
| *B01J 27/045* | (2006.01) |
| *B01J 27/10* | (2006.01) |
| *B01J 27/12* | (2006.01) |
| *B01J 27/13* | (2006.01) |
| *B01J 29/90* | (2006.01) |
| *C07C 5/41* | (2006.01) |
| *B01J 29/62* | (2006.01) |
| *B01J 38/64* | (2006.01) |
| *B01J 38/48* | (2006.01) |
| *B01J 38/02* | (2006.01) |
| *B01J 38/12* | (2006.01) |
| *B01J 37/06* | (2006.01) |
| *B01J 37/08* | (2006.01) |
| *B01J 37/24* | (2006.01) |
| *B01J 37/26* | (2006.01) |
| *B01J 37/30* | (2006.01) |
| *B01J 38/14* | (2006.01) |
| *B01J 38/54* | (2006.01) |
| *B01J 37/00* | (2006.01) |
| *B01J 37/02* | (2006.01) |
| *C07C 5/32* | (2006.01) |
| *C10G 35/095* | (2006.01) |
| *C10G 45/70* | (2006.01) |

(52) U.S. Cl.
CPC . *C10G 2300/4081* (2013.01); *C10G 2400/30* (2013.01)

(56) References Cited

U.S. PATENT DOCUMENTS

| | | | | |
|---|---|---|---|---|
| 3,959,382 A * | 5/1976 | Yeh | ............ | B01J 23/96 502/25 |
| 4,164,481 A * | 8/1979 | Ma | ............ | B01J 23/96 502/25 |
| 4,456,527 A | 6/1984 | Buss et al. | | |
| 4,507,397 A * | 3/1985 | Buss | ............ | B01J 23/96 208/140 |
| 4,678,764 A * | 7/1987 | Le | ............ | B01J 29/90 208/111.35 |
| 4,810,683 A * | 3/1989 | Cohn | ............ | B01J 29/90 208/140 |
| 4,826,792 A * | 5/1989 | Le | ............ | B01J 29/90 208/111.15 |
| 4,925,819 A * | 5/1990 | Fung | ............ | B01J 29/62 208/140 |
| 4,937,215 A * | 6/1990 | Murakawa | ............ | B01J 29/90 208/140 |
| 4,987,109 A | 1/1991 | Kao et al. | | |
| 5,196,631 A | 3/1993 | Murakawa et al. | | |
| RE34,250 E * | 5/1993 | Van Leirsburg | ............ | B01J 29/90 208/140 |
| 5,260,238 A * | 11/1993 | Murakawa | ............ | B01J 38/54 208/140 |
| 5,389,235 A | 2/1995 | Russ et al. | | |
| 5,401,365 A | 3/1995 | Chen et al. | | |
| 5,401,386 A | 3/1995 | Morrison et al. | | |
| 5,527,750 A * | 6/1996 | Haun | ............ | B01J 29/90 502/20 |
| 5,756,414 A * | 5/1998 | Huang | ............ | B01J 29/62 208/140 |
| 5,914,028 A * | 6/1999 | Wilson | ............ | B01J 8/008 208/134 |
| 6,190,539 B1 | 2/2001 | Holtermann et al. | | |
| 6,207,042 B1 * | 3/2001 | Holtermann | ............ | B01J 29/064 208/135 |
| 6,406,614 B1 | 6/2002 | Tiedtke et al. | | |
| 6,518,470 B1 | 2/2003 | Fukunaga et al. | | |
| 6,812,180 B2 | 11/2004 | Fukunaga | | |
| 7,037,871 B1 * | 5/2006 | Galperin | ............ | B01J 29/90 502/34 |
| 7,153,801 B2 | 12/2006 | Wu | | |
| 7,932,425 B2 | 4/2011 | Blessing et al. | | |
| 8,664,144 B2 | 3/2014 | Wu | | |
| 8,716,161 B2 | 5/2014 | Wu | | |
| 8,912,108 B2 | 12/2014 | Wu | | |
| 2002/0065443 A1 | 5/2002 | Williams et al. | | |
| 2018/0065115 A1 | 3/2018 | Alvez-Manoli | | |

OTHER PUBLICATIONS

McVicker et al., entitled "*Effect of Sulfur on the Performance and on the Particle Size and Location of Platinum in Pt/KL Hexane Aromatization Catalysts,*" Journal of Catalysis, 1993, vol. 139, pp. 48-61.

International Search Report and the Written Opinion of the International Searching Authority in PCT/US2017/066254 dated Apr. 17, 2018, 23 pages.

* cited by examiner

METHODS FOR REGENERATING SULFUR-CONTAMINATED AROMATIZATION CATALYSTS

FIELD OF THE INVENTION

The present disclosure concerns methods for the regeneration of spent or deactivated catalysts, and more particularly relates to the regeneration of sulfur-contaminated catalysts containing a transition metal, such as a group 10 transition metal, and a catalyst support.

BACKGROUND OF THE INVENTION

The catalytic conversion of non-aromatic hydrocarbons into aromatic compounds, often referred to as aromatization or reforming, is an important industrial process that may be used to produce benzene, toluene, xylenes, and the like. The aromatization or reforming process often is conducted in a reactor system that may contain one or more reactors containing transition metal based catalysts. These catalysts may increase the selectivity to and/or the yield of the desired aromatic compounds. However, these catalysts are highly sensitive to sulfur, and exposure to even very low concentrations of sulfur may cause rapid deactivation of the catalyst.

Because of their commercial importance and the expense incurred in producing fresh catalyst to replace sulfur-contaminated catalyst, there is an ongoing need for improved methods of restoring catalytic activity to sulfur-contaminated aromatization catalysts. Accordingly, it is to this end that the present disclosure is principally directed.

SUMMARY OF THE INVENTION

Methods for regenerating sulfur-contaminated catalysts comprising a transition metal and a catalyst support are disclosed and described herein. One such method for regenerating a sulfur-contaminated catalyst may comprise (1) washing the sulfur-contaminated catalyst with an aqueous solution, the aqueous solution optionally comprising an alkali metal, to produce a washed catalyst; and (2) contacting the washed catalyst with a halogen solution comprising chlorine, fluorine, or mixtures thereof, to produce a halogenated catalyst. Optionally, the method may further comprise a carbon burn step (prior to the washing step) in which the sulfur-contaminated catalyst is contacted with a decoking gas stream comprising oxygen, or the method may further comprise a carbon burn step (after the washing step) in which the washed catalyst is contacted with a decoking gas stream comprising oxygen.

Also disclosed herein are various processes for reforming hydrocarbons. An illustrative process may comprise (A) contacting a hydrocarbon feed with an aromatization catalyst comprising a transition metal and a catalyst support under reforming conditions in a reactor system to produce an aromatic product; (B) contacting a sulfur-contaminated hydrocarbon feed with the aromatization catalyst for a time period sufficient to form a sulfur-contaminated catalyst; (C) washing the sulfur-contaminated catalyst with an aqueous solution to produce a washed catalyst, the aqueous solution optionally comprising an alkali metal; and (D) contacting the washed catalyst with a halogen solution comprising chlorine, fluorine, or mixtures thereof, to produce a halogenated catalyst.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

Figure 1:
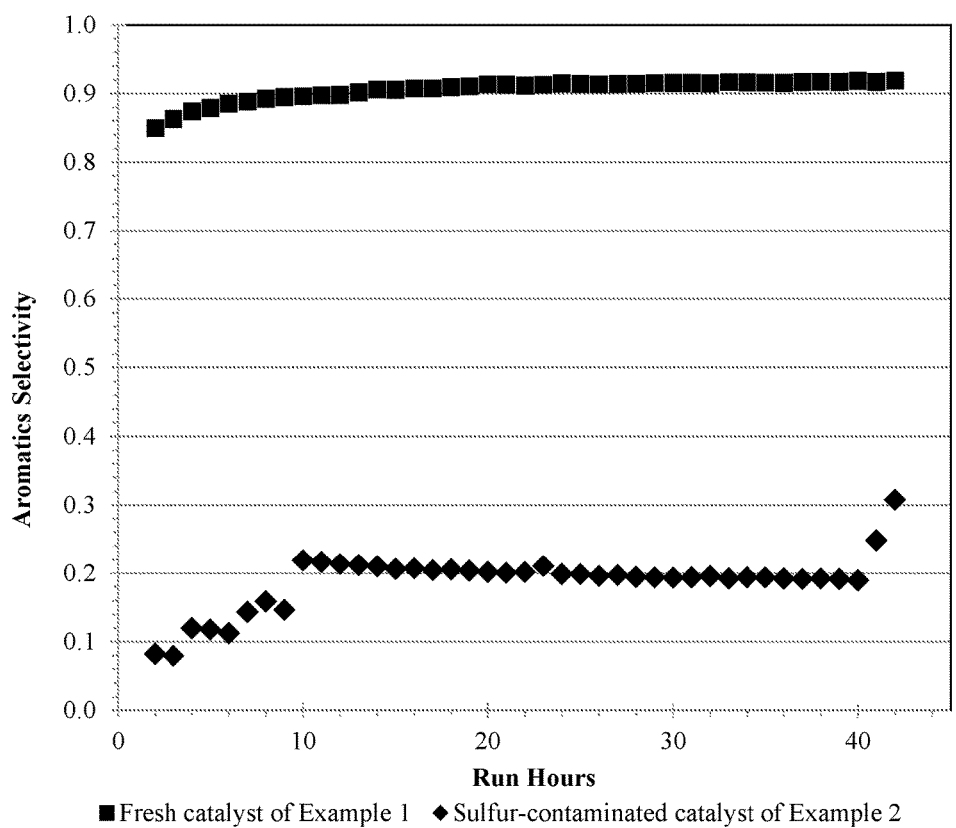
FIG. 1 presents a plot of the aromatics selectivity versus reaction time for the fresh catalyst of Example 1 and the sulfur-contaminated catalyst of Example 2.

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, $2^{nd}$ Ed (1997), may be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter are described such that, within particular aspects, a combination of different features may be envisioned. For each and every aspect and each and every feature disclosed herein, all combinations that do not detrimentally affect the designs, compositions, processes, or methods described herein are contemplated with or without explicit description of the particular combination. Additionally, unless explicitly recited otherwise, any aspect or feature disclosed herein may be combined to describe inventive designs, compositions, processes, or methods consistent with the present disclosure.

In this disclosure, while compositions and methods are often described in terms of "comprising" various components or steps, the compositions and methods may also "consist essentially of" or "consist of" the various components or steps, unless stated otherwise.

The terms "a," "an," and "the" are intended to include plural alternatives, e.g., at least one. For instance, the disclosure of "a transition metal" or "an alkali metal" is meant to encompass one, or mixtures or combinations of more than one, transition metal or alkali metal, unless otherwise specified.

Various catalysts are described herein. A "sulfur-contaminated" catalyst generally refers to a catalyst with sufficient sulfur contamination to result in unacceptable performance in one or more of catalyst activity, hydrocarbon feed conversion, yield to a desired product(s), selectivity to a desired product(s), or an operating parameter, such as output/production rate or reforming temperature, although the determination that a catalyst is "sulfur-contaminated" is not limited only to these features. In some aspects, the "fresh" catalyst may have an activity X, the sulfur-contaminated catalyst may have an activity Z, and a "regenerated" catalyst or a "reactivated" catalyst may have an activity Y, such that Z<Y<X. Such catalyst activity comparisons (and other reforming performance characteristics) are meant to use the same production run (batch) of catalyst, tested on the same equipment, and under the same test method and conditions. The "regenerated" catalyst encompasses catalysts regenerated using—at a minimum—the washing step and halogenation step described herein, while the "reactivated" catalyst is the "regenerated" catalyst that has been subjected to a reduction step (e.g., using hydrogen). As would be recognized by one of skill in the art in view of this disclosure, the "regenerated" catalyst is a generic term; it includes a catalyst that has been washed and halogenated (a "halogenated" catalyst), and is the same as a halogenated catalyst if other optional regeneration steps described herein are not used, but also encompasses catalysts that have been subjected to at least one of a carbon burn step, a drying step, a calcination step, or any combination thereof, in addition to the washing step and the halogenation step. Thus, for example, the "regenerated" catalyst encompasses (i) the "halogenated" catalyst, as well as (ii) a halogenated catalyst that has been subjected to an optional drying and/or calcining step, as well as (iii) a sulfur-contaminated catalyst that has been subjected to a washing step and a halogenation step and an optional carbon burn step at any suitable point within the process (e.g., carbon burn before washing, carbon burn after washing), and so forth.

The amounts of any components or materials present on the catalysts described herein (e.g., fresh catalyst, sulfur-contaminated catalyst, regenerated catalyst, or reactivated catalyst) are on a weight basis, such as wt. % or ppmw (ppm by weight), unless otherwise specified. These components or materials may include, for instance, the amount of sulfur, the amount of carbon, the amount of fluorine, the amount of chlorine, the amount of alkali metal, the amount of barium, the amount of platinum, and so forth. Moreover, these amounts are based on a "dry" catalyst, wherein the respective catalyst (e.g., fresh catalyst, sulfur-contaminated catalyst, regenerated catalyst, or reactivated catalyst) has been dried to a solvent/water content of less than 5 wt. %.

Generally, groups of elements are indicated using the numbering scheme indicated in the version of the periodic table of elements published in *Chemical and Engineering News*, 63(5), 27, 1985. In some instances, a group of elements may be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure (general or specific) presented is intended to encompass all conformational isomers, regioisomers, stereoisomers, and mixtures thereof that may arise from a particular set of substituents, unless otherwise specified. The name or structure (general or specific) also encompasses all enantiomers, diastereomers, and other optical isomers (if there are any) whether in enantiomeric or racemic forms, as well as mixtures of stereoisomers, as would be recognized by a skilled artisan, unless otherwise specified. For example, a general reference to hexane includes n-hexane, 2-methyl-pentane, 3-methyl-pentane, 2,2-dimethyl-butane, and 2,3-dimethyl-butane; and a general reference to a butyl group includes a n-butyl group, a sec-butyl group, an iso-butyl group, and a t-butyl group.

In one aspect, a chemical "group" may be defined or described according to how that group is formally derived from a reference or "parent" compound, for example, by the number of hydrogen atoms removed from the parent compound to generate the group, even if that group is not literally synthesized in such a manner. These groups may be utilized as substituents or coordinated or bonded to metal atoms. By way of example, an "alkyl group" formally may be derived by removing one hydrogen atom from an alkane. The disclosure that a substituent, ligand, or other chemical moiety may constitute a particular "group" implies that the well-known rules of chemical structure and bonding are followed when that group is employed as described. When describing a group as being "derived by," "derived from," "formed by," or "formed from," such terms are used in a formal sense and are not intended to reflect any specific synthetic methods or procedures, unless specified otherwise or the context requires otherwise.

Various numerical ranges are disclosed herein. When a range of any type is disclosed or claimed herein, the intent is to disclose or claim individually each possible number that such a range could reasonably encompass, including end points of the range as well as any sub-ranges and combinations of sub-ranges encompassed therein, unless otherwise specified. As a representative example, the present application discloses that a catalyst may contain Cl and F at a molar ratio of Cl:F in a range from about 0.5:1 to about 4:1 in certain aspects. By a disclosure that the molar ratio of Cl:F may be in a range from about 0.5:1 to about 4:1, the intent is to recite that the molar ratio may be any molar ratio within the range and, for example, may be equal to about 0.5:1, about 0.6:1, about 0.7:1, about 0.8:1, about 0.9:1, about 1:1, about 2:1, about 3:1, or about 4:1. Additionally, the molar ratio of Cl:F may be within any range from about 0.5:1 to about 4:1 (for example, the molar ratio may be in a range from about 0.5:1 to about 2:1), and this also includes any combination of ranges between about 0.5:1 and about 4:1. Likewise, all other ranges disclosed herein should be interpreted in a manner similar to this example.

The term "substituted" when used to describe a group, for example, when referring to a substituted analog of a particular group, is intended to describe any non-hydrogen moiety that formally replaces a hydrogen atom in that group, and is intended to be non-limiting. A group or groups may also be referred to herein as "unsubstituted" or by equivalent terms such as "non-substituted," which refers to the original group in which a non-hydrogen moiety does not replace a hydrogen atom within that group. Unless otherwise specified, "substituted" is intended to be non-limiting and include inorganic substituents or organic substituents as understood by one of ordinary skill in the art.

As used herein, the term "hydrocarbon" refers to a compound containing only carbon and hydrogen atoms. Other identifiers may be utilized to indicate the presence of particular groups, if any, in the hydrocarbon (e.g., halogenated hydrocarbon indicates that the presence of one or more halogen atoms replacing an equivalent number of hydrogen atoms in the hydrocarbon).

An "aromatic" compound is a compound containing a cyclically conjugated double bond system that follows the Hückel (4n+2) rule and contains (4n+2) pi-electrons, where n is an integer from 1 to 5. Aromatic compounds include "arenes" (hydrocarbon aromatic compounds, e.g., benzene, toluene, and xylenes) and "heteroarenes" (heteroaromatic compounds formally derived from arenes by replacement of one or more methine (—C=) carbon atoms of the cyclically conjugated double bond system with a trivalent or divalent heteroatoms, in such a way as to maintain the continuous pi-electron system characteristic of an aromatic system and a number of out-of-plane pi-electrons corresponding to the Hückel rule (4n+2)). As disclosed herein, the term "substituted" may be used to describe an aromatic group, arene, or heteroarene, wherein a non-hydrogen moiety formally replaces a hydrogen atom in the compound, and is intended to be non-limiting, unless specified otherwise.

As used herein, the term "alkane" refers to a saturated hydrocarbon compound. Other identifiers may be utilized to indicate the presence of particular groups, if any, in the alkane (e.g., halogenated alkane indicates that the presence of one or more halogen atoms replacing an equivalent number of hydrogen atoms in the alkane). The term "alkyl group" is used herein in accordance with the definition specified by IUPAC: a univalent group formed by removing a hydrogen atom from an alkane. The alkane or alkyl group may be linear or branched unless otherwise specified.

A "cycloalkane" is a saturated cyclic hydrocarbon, with or without side chains, for example, cyclobutane, cyclopentane, cyclohexane, methyl cyclopentane, and methyl cyclohexane. Other identifiers may be utilized to indicate the presence of particular groups, if any, in the cycloalkane (e.g., halogenated cycloalkane indicates that the presence of one or more halogen atoms replacing an equivalent number of hydrogen atoms in the cycloalkane).

The term "halogen" has its usual meaning. Examples of halogens include fluorine, chlorine, bromine, and iodine.

The terms "contact," "contacting," and the like, are used herein to refer to materials or components that may be blended, mixed, slurried, dissolved, reacted, treated, compounded, or otherwise contacted or combined in some other manner or by any suitable method. The materials or components may be contacted together in any order, in any manner, and for any length of time, unless otherwise specified.

Molar selectivity's are defined as:

$$\text{Benzene selectivity: } S_{Bz} = \frac{\dot{n}_{Bz,prod}}{\dot{n}_{convC6,feed} - \dot{n}_{convC6,prod}} \quad \text{Eq. 1}$$

$$\text{Toluene selectivity: } S_{Tol} = \frac{\dot{n}_{Tol,prod}}{\dot{n}_{convC7,feed} - \dot{n}_{convC7,prod}} \quad \text{Eq. 2}$$

$$\text{Benzene + Toluene selectivity: } S_{Bz+Tol} = \frac{\dot{n}_{Bz,prod} + \dot{n}_{Tol,prod}}{\dot{n}_{convC6,C7,feed} - \dot{n}_{convC6,C7,prod}} \quad \text{Eq. 3}$$

$$\text{Aromatics selectivity: } S_{arom} = \frac{\dot{n}_{Bz,prod} + \dot{n}_{Tol,prod} + \dot{n}_{CB+arom,prod}}{\dot{n}_{convC6-C8+,feed} - \dot{n}_{convC6-C8+,prod}} \quad \text{Eq. 4}$$

Conversion is defined as the number of moles converted per mol of "convertible" components fed:

$$\text{C6 conversion: } X_{C6} = \frac{\dot{n}_{convC6,feed} - \dot{n}_{convC6,prod}}{\dot{n}_{convC6,feed}} \quad \text{Eq. 5}$$

$$\text{C7 conversion: } X_{C7} = \frac{\dot{n}_{convC7,feed} - \dot{n}_{convC7,prod}}{\dot{n}_{convC7,feed}} \quad \text{Eq. 6}$$

$$\text{C6 + C7 conversion: } X_{C6+C7} = \frac{\dot{n}_{convC6,feed} + \dot{n}_{convC7,feed} - \dot{n}_{convC6,prod} - \dot{n}_{convC7,prod}}{\dot{n}_{convC6,feed} + \dot{n}_{convC7,feed}} \quad \text{Eq. 7}$$

Although any methods and materials similar or equivalent to those described herein may be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Disclosed herein are methods for regenerating a sulfur-contaminated catalyst, such as a sulfur-contaminated aromatization catalyst. Related reforming processes also are disclosed.

Methods for Regenerating Sulfur-Contaminated Catalysts

Various methods for regenerating sulfur-contaminated catalysts comprising a transition metal and a catalyst support are disclosed and described. One such method for regenerating a sulfur-contaminated catalyst may comprise (or consist essentially of, or consist of):

(1) washing the sulfur-contaminated catalyst with an aqueous solution, the aqueous solution optionally comprising an alkali metal, to produce a washed catalyst; and (2) contacting the washed catalyst with a halogen solution comprising chlorine, fluorine, or mixtures thereof, to produce a halogenated catalyst.

Generally, the features of any of the methods disclosed herein (e.g., the sulfur-contaminated catalyst, the transition metal, the catalyst support, the aqueous solution, the halogen solution, the conditions under which the washing step is conducted, and the conditions under which the halogenation step is conducted, among others) are independently described herein, and these features may be combined in any combination to further describe the disclosed methods. Moreover, other process steps may be conducted before, during, and/or after any of the steps listed in the disclosed methods, unless stated otherwise. Additionally, regenerated (e.g., halogenated) catalysts and reactivated catalysts produced in accordance with any of the disclosed methods/processes are within the scope of this disclosure and are encompassed herein.

The steps of these methods that utilize the aqueous solution often may be referred to as washing steps, while the steps of these methods that utilize a halogen solution often may be referred to as halogenation steps. Any compositional attributes of the aqueous solution and the halogen solution are meant to refer to the respective incoming aqueous solution and halogen solution, prior to contacting the catalyst, unless expressly stated otherwise. As one of skill in the art would readily recognize, the outgoing aqueous solution and halogen solution, after contacting the catalyst, may vary significantly in composition from the respective incoming aqueous solution and the halogen solution.

Referring now to step (1), also referred to as the washing step, the sulfur-contaminated catalyst may be washed with any suitable aqueous solution, optionally comprising an alkali metal, resulting in a washed catalyst. The alkali metal in step (1) may be any Group 1 element. For instance, the aqueous solution may comprise an alkali metal, and the alkali metal may comprise (or consist essentially of, or consist of) sodium, potassium, rubidium, or cesium, as well as any combination thereof. In some aspects, the alkali metal may comprise (or consist essentially of, or consist of) sodium; alternatively, potassium; alternatively, rubidium; or alternatively, cesium.

The aqueous solution may contain the alkali metal (or metals) in any suitable form, but often, the aqueous solution contains a salt of the alkali metal. Illustrative salts may include, but are not limited to, chlorides, fluorides, bromides, iodides, nitrates, and the like, as well as combinations thereof. In particular aspects of this invention, the aqueous solution in the washing step may comprise an alkali metal halide salt or an alkali metal chloride salt, such as potassium chloride, rubidium chloride, or cesium chloride, as well as any mixture or combination thereof.

In addition to water and the optional alkali metal, the aqueous solution may contain other components, as would be recognized by those of skill in the art. However, in some aspects, the washing step may comprise contacting the sulfur-contaminated catalyst with an aqueous solution consisting essentially of or consisting of water, or consisting essentially of or consisting of an alkali metal salt and water, or consisting essentially of or consisting of an alkali metal salt and deionized water. In these and other aspects, the aqueous solution may be substantially free of a basic compound (e.g., a hydroxide) and/or substantially free of ammonia or any ammonium-containing compounds. In these circumstances, "substantially free" is meant to contain less than 100 ppmw (ppm by weight), independently, of any of these materials, and more typically, less than 75 ppmw, less than 50 ppmw, less than 25 ppmw, or less than 10 ppmw. Therefore, it is contemplated that the individual amount of any of these materials in the aqueous solution may be in range from about 0.1 ppmw to about 100 ppmw, from about 0.1 ppmw to about 75 ppmw, from about 1 ppmw to about 100 ppmw, from about 1 ppmw to about 75 ppmw, from about 0.1 ppmw to about 50 ppmw, from about 1 ppmw to about 50 ppmw, or from about 1 ppmw to about 25 ppmw. While not wishing to be bound by theory, it is believed that it may be beneficial to have substantially none of these materials present during the washing step in the disclosed methods for regenerating a sulfur-contaminated catalyst, as these materials may adversely affect one or more of the catalyst activity, catalyst selectivity, catalyst lifetime and/or catalyst deactivation. Moreover, although not required, the aqueous solution may be substantially free of sodium or any sodium-containing compound, i.e., may contain less than 100 ppmw (ppm by weight) of sodium or sodium-containing compounds. As above, it is contemplated that the amount may be, for instance, less than 75 ppmw, less than 50 ppmw, less than 25 ppmw, in a range from about 0.1 ppmw to about 100 ppmw, in a range from about 0.1 ppmw to about 75 ppmw, or in a range from about 1 ppmw to about 75 ppmw, and the like. Thus, in some aspects, the alkali metal used in the washing step is not sodium, but is one or more of potassium, rubidium, and/or cesium.

In the washing step, the pH of the aqueous solution is not limited to any particular range. Generally, however, the pH may be in the 6-8 range, depending upon the alkali metal salt utilized and its respective concentration.

While not being limited thereto, the amount of the alkali metal (if used) in the aqueous solution often may be less than about 5 M (mole/L). For instance, the aqueous solution may have a concentration of the alkali metal of less than about 1 M, less than about 0.75 M, less than about 0.5 M, less than about 0.3 M, less than about 0.25 M, or less than about 0.2 M. Therefore, suitable ranges for the concentration of the alkali metal may include, but are not limited to, the following ranges: from about 0.01 M to about 5 M, from about 0.01 M to about 1 M, from about 0.01 M to about 0.5 M, from about 0.01 M to about 0.25 M, from about 0.05 M to about 2 M, from about 0.05 M to about 1 M, from about 0.05 M to about 0.5 M, from about 0.05 M to about 0.25 M, from about 0.1 M to about 5 M, from about 0.1 M to about 1 M, or from about 0.1 M to about 0.5 M, and the like.

The washing step, optionally containing the alkali metal, may be conducted at a variety of temperatures and time periods. For instance, the washing step may be conducted at a washing temperature in a range from about 15° C. to about 95° C.; alternatively, from about 15° C. to about 80° C.; alternatively, from about 15° C. to about 70° C.; alternatively, from about 15° C. to about 65° C.; alternatively, from about 20° C. to about 95° C.; alternatively, from about 20° C. to about 80° C.; alternatively, from about 20° C. to about 70° C.; alternatively, from about 20° C. to about 50° C.; alternatively, from about 30° C. to about 80° C.; alternatively, from about 30° C. to about 70° C.; alternatively, from about 30° C. to about 50° C.; alternatively, from about 25° C. to about 55° C.; or alternatively, from about 30° C. to about 45° C. In these and other aspects, these temperature ranges also are meant to encompass circumstances where the washing step is conducted at a series of different temperatures, instead of at a single fixed temperature, falling within the respective ranges.

The washing step, optionally containing the alkali metal, may be conducted by performing more than one washing cycle, such as from 1 to 4 washing cycles, from 2 to 8 washing cycles, or from 2 to 4 washing cycles. Thus, for example, the washing step may comprise from 1 to 4 washing cycles, from 2 to 8 washing cycles, or from 2 to 4 washing cycles, with each washing cycle, independently, ranging from about 1 minute to about 6 hours, from about 5 minutes to about 2 hours, from about 10 minutes to about 45 minutes, or from about 10 minutes to about 30 minutes, and so forth.

The duration of a single washing cycle, optionally containing the alkali metal, is not limited to any particular period of time. Hence, a washing cycle may be conducted, for example, in a time period ranging from as little as 1-5 minutes to as long as 2-4 hours, 6-8 hours, or more. The appropriate washing cycle time may depend upon, for example, the washing temperature, the amount of alkali metal in the aqueous solution, and the number of washing cycles, among other variables. Generally, however, the washing cycle step may be conducted in a time period that may be in a range from about 1 minute to about 6 hours, such as, for example, from about 1 minute to about 2 hours, from about 5 minutes to about 2 hours, from about 5 minutes to about 1 hour, from about 10 minutes to about 1 hour, from about 5 minutes to about 45 minutes, from about 10 minutes to about 45 minutes, or from about 10 minutes to about 30 minutes.

Generally, the amount of the aqueous solution—optionally containing the alkali metal—used in the washing step (or in each washing cycle) relative to the amount of the sulfur-contaminated catalyst is not particularly limited. In one aspect, for instance, the ratio of the weight of the aqueous solution to the weight of the sulfur-contaminated catalyst may fall within a range of from about 0.4:1 to about 50:1, or from about 0.5:1 to about 25:1. In another aspect, the ratio of the weight of the aqueous solution to the weight of the sulfur-contaminated catalyst may range from about 0.4:1 to about 10:1, or from about 0.5:1 to about 10:1. In yet another aspect, the ratio of the weight of the aqueous solution to the weight of the sulfur-contaminated catalyst may range from about 0.5:1 to about 8:1, or from about 0.5:1 to about 5:1. In still another aspect, the ratio of the weight of the aqueous solution to the weight of the sulfur-contaminated catalyst may range from about 1:1 to about 15:1, or from about 1:1 to about 5:1.

The washing step, optionally containing the alkali metal, may be conducted using any suitable technique and equipment. For instance, the sulfur-contaminated catalyst may be placed into a vessel or tank, and then filled with enough of the aqueous solution to exceed the level of the sulfur-contaminated catalyst in the vessel or tank. Optionally, agitation may be provided in the vessel and tank to increase the contact between the sulfur-contaminated catalyst and the aqueous solution. Alternatively, the sulfur-contaminated catalyst may be placed in a fixed or packed bed arrangement, and the aqueous solution, optionally containing the alkali metal, may be contacted with the sulfur-contaminated catalyst by flowing the aqueous solution through the bed of the sulfur-contaminated catalyst. As would be recognized by those of skill in the art, other suitable techniques and equipment may be employed for the washing step, and such techniques and equipment are encompassed herein.

Although not required, the washing step may be performed by one or more washing cycles using the aqueous solution containing an alkali metal, and then completed by performing one or more washing cycles without the alkali metal. Alternatively, the washing step may be performed by one or more washing cycles using the aqueous solution without the alkali metal, and then completed by performing one or more washing cycles with the alkali metal. Alternatively, the washing step may be performed by one or more washing cycles using the aqueous solution without the alkali metal, followed by performing one or more washing cycles with the alkali metal, and then completed by performing one or more washing cycles without the alkali metal. Independently, the washing conditions used with and without the alkali metal may be any washing step conditions described herein.

In step (1) of the methods for regenerating a sulfur-contaminated catalyst disclosed herein, the sulfur-contaminated catalyst may be washed with an aqueous solution containing an alkali metal to produce an alkali metal "enriched" washed catalyst. In effect, the washing step may remove sulfur from the contaminated catalyst, while concurrently enriching the sulfur-contaminated catalyst with any suitable or desired amount of alkali metal, wherein the amount of enrichment is the difference in the amount of the alkali metal in the washed catalyst after the washing step versus the amount of the alkali metal in the sulfur-contaminated catalyst. While not being limited thereto, the washing step may enrich the sulfur-contaminated catalyst with from about 0.05 moles to about 1.5 moles of the alkali metal per kg of the sulfur-contaminated catalyst (or per kg of the washed catalyst); alternatively, from about 0.05 moles to about 1 mole of the alkali metal per kg of the sulfur-contaminated catalyst (or per kg of the washed catalyst); alternatively, from about 0.05 moles to about 0.7 moles of the alkali metal per kg of the sulfur-contaminated catalyst (or per kg of the washed catalyst); alternatively, from about 0.1 moles to about 1.2 moles of the alkali metal per kg of the sulfur-contaminated catalyst (or per kg of the washed catalyst); alternatively, from about 0.1 moles to about 0.9 moles of the alkali metal per kg of the sulfur-contaminated catalyst (or per kg of the washed catalyst); alternatively, from about 0.2 moles to about 0.8 moles of the alkali metal per kg of the sulfur-contaminated catalyst (or per kg of the washed catalyst); or alternatively, from about 0.3 moles to about 0.7 moles of the alkali metal per kg of the sulfur-contaminated catalyst (or per kg of the washed catalyst).

As an example, a sulfur-contaminated catalyst (containing no cesium) may be washed with an aqueous solution containing a cesium salt (in one or more washing cycles conducted at any temperature, washing time, and relative amount of the aqueous solution disclosed herein) to produce a cesium enriched catalyst containing about 0.5 moles of cesium per kg of the sulfur-contaminated catalyst (or about 0.5 moles of cesium per kg of the washed catalyst). As another example, a sulfur-contaminated catalyst (such as a contaminated catalyst comprising platinum and a zeolitic support comprising a KL-zeolite, further containing about 3 moles of potassium per kg of the contaminated catalyst) may be washed with an aqueous solution containing a potassium salt (in one or more washing cycles conducted at any temperature, washing time, and relative amount of the aqueous solution disclosed herein) to produce a potassium enriched washed catalyst containing about 3.1 moles of potassium per kg of the sulfur-contaminated catalyst (or about 3.1 moles per kg of the potassium enriched washed catalyst).

In addition to removing sulfur and optionally increasing the alkali metal content during the washing step, the level of sodium may be reduced, assuming that the sulfur-contaminated catalyst contains sodium and the aqueous solution does not. In these circumstances, the resultant washed catalyst may contain less than about 0.35 wt. % sodium, or less than about 0.3 wt. % sodium, based on the weight of the washed catalyst. In some aspects, the amount of sodium in the washed catalyst may range from 0 wt. % to about 0.35 wt. %, from 0 wt. % to about 0.3 wt. %, from about 0.03 wt. % to about 0.35 wt. %, or from about 0.05 wt. % to about 0.3 wt. % sodium, based on the weight of the washed catalyst. These weight percentages are based on the weight of the washed catalyst on a "dry" basis.

While not limited thereto, the amount of sulfur in the sulfur-contaminated catalyst often may be at least about 100 ppmw, at least about 125 ppmw, or at least about 150 ppmw. Illustrative and non-limiting ranges include from about 100 ppmw to about 1000 ppmw, from about 100 ppmw to about 500 ppmw, or from about 125 ppmw to about 1250 ppmw sulfur, based on the weight of the sulfur-contaminated catalyst. As described herein, these weight percentages are based on the weight of the "dry" sulfur-contaminated catalyst.

The washing step generally is very effective at removing sulfur from the sulfur-contaminated catalyst. Often, the amount of sulfur (in ppmw) is reduced by at least about 20%, by at least about 25%, by at least about 30%, or by at least about 35%, and often up to 70%, 80%, 90%, or more. Thus, from about 20% to about 90%, from about 25% to about 90%, from about 35% to about 90%, or from about 30% to about 80%, of the sulfur may be removed, based on the difference in the amount of sulfur (in ppmw) in the washed catalyst (or the halogenated catalyst) and the amount of sulfur (in ppmw) in the sulfur-contaminated catalyst. As above, these amounts of sulfur are determined on the respective "dry" catalysts.

While not being limited thereto, the sulfur-contaminated catalyst often may contain from greater than 0 wt. % to about 5 wt. % chlorine, from about 0.05 wt. % to about 2 wt. % chlorine, or from about 0.1 wt. % to about 1 wt. % chlorine. Additionally or alternatively, the sulfur-contaminated may contain from greater than 0 wt. % to about 5 wt. % fluorine, from about 0.05 wt. % to about 2 wt. % fluorine, or from about 0.1 wt. % to about 1 wt. % fluorine. Additionally or alternatively, the sulfur-contaminated catalyst may contain less than about 0.1 wt. % of barium, less than about 0.01 wt. % barium, or no barium (no measurable amount).

As those of skill in the art will readily recognize, a specific or target amount of sulfur removed via the washing step base may be accomplished by various combinations of conditions that may be used in step (1). Once a desired level of sulfur removal is selected, this result may be achieved by many different combinations of the number of washing cycles, the washing time, the washing temperature, the molar concentration of the alkali metal (if used) in the aqueous solution, the relative amount of aqueous solution used based on the weight of the sulfur-contaminated catalyst, and so forth.

Once the washed catalyst has been produced in step (1), optionally, the washed catalyst may be dried and/or calcined (as further described hereinbelow) prior to step (2). If both drying and calcining are performed, typically the washed catalyst is dried and then calcined.

In step (2) of the method for regenerating a sulfur-contaminated catalyst (also referred to as the halogenation step), the washed catalyst may be contacted with a halogen solution comprising chlorine, fluorine, or mixtures thereof, to produce a halogenated catalyst. It may be beneficial to add a halogen (or halogens) back to the catalyst after the washing step in order to restore catalyst activity and performance—a washing step alone may be insufficient. In one aspect of this invention, the halogen solution may comprise (or consist essentially of, or consist of) a chlorine-containing compound, a fluorine-containing compound, or a mixture thereof, and water, while in another aspect, the halogen solution may comprise (or consist essentially of, or consist of) a chlorine-containing compound, a fluorine-containing compound, or a mixture thereof, and a hydrocarbon solvent. When a hydrocarbon solvent is used, non-polar aliphatic hydrocarbons such as cyclohexane, isobutane, n-butane, n-pentane, isopentane, neopentane, n-hexane, n-heptane, and the like, or combinations thereof, may be used. Additionally or alternatively, an aromatic compound may be used, non-limiting examples of which include toluene, benzene, xylene, and the like, or combinations thereof.

Suitable fluorine-containing compounds may include, but are not limited to, hydrofluoric acid, 2,2,2-trifluoroethanol, tetrafluoroethylene, carbon tetrafluoride, carbon trifluoride, fluoromethane, heptafluoropropane, decafluorobutane, hexafluoroisopropanol, tetrafluoropropanol, pentafluoropropanol, hexafluorophenylpropanol, perfluorobutyl alcohol, hexafluor-2-propanol, pentafluoro-1-propanol, tetrafluoro-1-propanol, 1,1,1,3,3,3-hexafluoro-2-propanol, 2,2,3,3,3-pentafluoro-1-propanol, ammonium fluoride, tetramethylammonium fluoride, tetraethylammonium fluoride, tetrapropylammonium fluoride, tetrabutylammonium fluoride, methyltriethylammonium fluoride, and the like, or any combination thereof. Other suitable fluorine-containing compounds may include arenes and alkyl-substituted arenes (e.g., benzene, toluene, and xylene) where at least one hydrogen atom is replaced with a F atom.

In another aspect, the fluorine-containing compound may comprise (or consist essentially of, or consist of) hydrofluoric acid, ammonium fluoride, tetramethylammonium fluoride, or a combination thereof; alternatively, hydrofluoric acid; alternatively, 2,2,2-trifluoroethanol; alternatively, tetrafluoroethylene; alternatively, carbon tetrafluoride; alternatively, carbon trifluoride; alternatively, fluoromethane; alternatively, heptafluoropropane; alternatively, decafluorobutane; alternatively, hexafluoroisopropanol; alternatively, tetrafluoropropanol; alternatively, pentafluoropropanol; alternatively, hexafluorophenylpropanol; alternatively, perfluorobutyl alcohol; alternatively, hexafluor-2-propanol; alternatively, pentafluoro-1-propanol; alternatively, tetrafluoro-1-propanol; alternatively, 1,1,1,3,3,3-hexafluoro-2-propanol; alternatively, 2,2,3,3,3-pentafluoro-1-propanol; alternatively, ammonium fluoride; alternatively, tetramethylammonium fluoride; alternatively, tetraethylammonium fluoride; alternatively, tetrapropylammonium fluoride; alternatively, tetrabutylammonium fluoride; or alternatively, methyltriethylammonium fluoride.

Suitable chlorine-containing compounds may include, but are not limited to, hydrochloric acid, carbon tetrachloride, tetrachloroethylene, chlorobenzene, methyl chloride, methylene chloride, chloroform, allyl chloride, trichloroethylene, a chloramine, a chlorine oxide, a chlorine acid, chlorine dioxide, dichlorine monoxide, dichlorine heptoxide, chloric acid, perchloric acid, ammonium chloride, tetramethylammonium chloride, tetraethylammonium chloride, tetrapropylammonium chloride, tetrabutylammonium chloride, methyltriethylammonium chloride, and the like, or any combination thereof. Other suitable chlorine-containing compounds may include arenes and alkyl-substituted arenes (e.g., benzene, toluene, and xylene) where at least one hydrogen atom is replaced with a Cl atom.

In another aspect, the chlorine-containing compound may comprise (or consist essentially of, or consist of) hydrochloric acid, ammonium chloride, tetramethylammonium chloride, or a combination thereof alternatively, hydrochloric acid; alternatively, carbon tetrachloride; alternatively, tetrachloroethylene; alternatively, chlorobenzene; alternatively, methyl chloride; alternatively, methylene chloride; alternatively, chloroform; alternatively, allyl chloride; alternatively, trichloroethylene; alternatively, a chloramine; alternatively, a chlorine oxide; alternatively, a chlorine acid; alternatively, chlorine dioxide; alternatively, dichlorine monoxide; alternatively, dichlorine heptoxide; alternatively, chloric acid; alternatively, perchloric acid; alternatively, ammonium chloride; alternatively, tetramethylammonium chloride; alternatively, tetraethylammonium chloride; alternatively, tetrapropylammonium chloride; alternatively, tetrabutylammonium chloride; or alternatively, methyltriethylammonium chloride.

In yet another aspect, the halogen solution may comprise (or consist essentially of, or consist of) water and a fluorine-containing compound, and the fluorine-containing compound may comprise hydrofluoric acid, ammonium fluoride, tetramethylammonium fluoride, or a combination thereof. In still another aspect, the solution may comprise (or consist essentially of, or consist of) water and hydrofluoric acid; alternatively, water and ammonium fluoride; or alternatively, water and tetramethylammonium fluoride.

Likewise, in another aspect, the halogen solution may comprise (or consist essentially of, or consist of) water and a chlorine-containing compound, and the chlorine-containing compound may comprise hydrochloric acid, ammonium chloride, tetramethylammonium chloride, or a combination thereof. In another aspect, the solution may comprise (or consist essentially of, or consist of) water and hydrochloric acid; alternatively, water and ammonium chloride; or alternatively, water and tetramethylammonium chloride.

Consistent with particular aspects of this invention, both chlorine and fluorine are present in the halogen solution. In such aspects, the halogen solution may comprise (or consist essentially of, or consist of) any suitable chlorine-containing compound (for example, ammonium chloride), any suitable fluorine-containing compound (for example, ammonium fluoride), and water. Alternatively, the halogen solution may comprise (or consist essentially of, or consist of) a chlorine/fluorine-containing compound (or chlorofluorocarbon), and any suitable solvent, for example, water or a hydrocarbon solvent.

The halogenation step may be conducted using any suitable technique and equipment, for example, to result in uniform distribution of the halogen (chlorine, fluorine, or both). For instance, the washed catalyst may be placed into a vessel or tank, and then filled with enough of the halogen solution (comprising the chlorine, fluorine, or both) to exceed the level of the catalyst in the vessel or tank. Optionally, agitation may be provided in the vessel and tank to increase the contact between the catalyst and the halogen-containing compound(s) within the solution. Alternatively, the washed catalyst may be placed in a fixed or packed bed arrangement, and the halogen solution may be contacted with the catalyst by flowing the halogen solution through the bed of the catalyst. Alternatively, the washed catalyst may be placed into a rotating drum, and the halogen solution (comprising chlorine, fluorine, or both) may be poured or sprayed onto the catalyst. Alternatively, the washed catalyst may be impregnated to incipient wetness with the halogen solution (comprising chlorine, fluorine, or both), wherein the pore filling or "incipient wetness" impregnation technique used is a method in which the halogen solution is mixed with the (generally dry) washed catalyst until the pores are filled. The definition of the end point of this method may vary somewhat from laboratory to laboratory so that an impregnated catalyst could have a completely dry appearance or a sticky snow-like appearance. However, typically there would not be any free-flowing liquid present when the incipient wetness method is employed. As would be recognized by those of skill in the art, other suitable techniques and equipment may be employed for the halogenation step, and such techniques and equipment are encompassed herein.

While not being limited thereto, the amount of fluorine (F) in the halogen solution often is less than about 15 wt. %. For instance, the halogen solution may comprise a concentration/amount of F of less than about 10 wt. %; alternatively, less than about 8 wt. %; alternatively, less than about 5 wt. %; or alternatively, less than about 3 wt. %. When present, suitable ranges for the concentration of F in the halogen solution may include, but are not limited to, the following ranges: from about 0.01 wt. % to about 10 wt. %, from about 0.1 wt. % to about 10 wt. %, from about 0.5 wt. % to about 10 wt. %, from about 1 wt. % to about 10 wt. %, from about 0.01 wt. % to about 8 wt. %, from about 0.1 wt. % to about 8 wt. %, from about 1 wt. % to about 8 wt. %, from about 0.01 wt. % to about 5 wt. %, from about 0.1 wt. % to about 5 wt. %, from about 0.5 wt. % to about 5 wt. %, or from about 1 wt. % to about 5 wt. %, and the like.

Likewise, the amount of chlorine (Cl) in the halogen solution often is less than about 15 wt. %. For instance, the halogen solution may comprise a concentration/amount of Cl of less than about 10 wt. %; alternatively, less than about 8 wt. %; alternatively, less than about 5 wt. %; or alternatively, less than about 3 wt. %. When present, suitable ranges for the concentration of Cl may include, but are not limited to, the following ranges: from about 0.01 wt. % to about 10 wt. %, from about 0.1 wt. % to about 10 wt. %, from about 0.5 wt. % to about 10 wt. %, from about 1 wt. % to about 10 wt. %, from about 0.01 wt. % to about 8 wt. %, from about 0.1 wt. % to about 8 wt. %, from about 1 wt. % to about 8 wt. %, from about 0.01 wt. % to about 5 wt. %, from about 0.1 wt. % to about 5 wt. %, from about 0.5 wt. % to about 5 wt. %, or from about 1 wt. % to about 5 wt. %, and the like.

The halogenation step may be conducted at a variety of temperatures and time periods. For instance, the halogenation step may be conducted at a halogenation temperature in a range from about 0° C. to about 95° C.; alternatively, from about 0° C. to about 80° C.; alternatively, from about 0° C. to about 50° C.; alternatively, from about 5° C. to about 95° C.; alternatively, from about 5° C. to about 80° C.; alternatively, from about 5° C. to about 50° C.; alternatively, from about 5° C. to about 35° C.; alternatively, from about 15° C. to about 80° C.; alternatively, from about 15° C. to about 50° C.; alternatively, from about 15° C. to about 35° C.; alternatively, from about 20° C. to about 95° C.; alternatively, from about 20° C. to about 50° C.; or alternatively, from about 20° C. to about 35° C. In these and other aspects, these temperature ranges also are meant to encompass circumstances where the halogenation step is conducted at a series of different temperatures, instead of at a single fixed temperature, falling within the respective ranges.

The duration of the halogenation step is not limited to any particular period of time. Hence, the halogenation step may be conducted, for example, in a time period ranging from as little as 1-5 minutes to as long as 12-24 hours, 36-48 hours, or more. The appropriate halogenation time may depend upon, for example, the halogenation temperature and the respective amounts of fluorine and chlorine in the solution, among other variables. Generally, however, the halogenation step may be conducted in a time period that may be in a range from about 1 minute to about 48 hours, such as, for example, from about 15 minutes to about 48 hours, from about 10 minutes to about 24 hours, from about 30 minutes to about 18 hours, from about 30 minutes to about 12 hours, from about 30 minutes to about 6 hours, from about 1 hour to about 10 hours, or from about 2 hours to about 8 hours.

If a drying step is performed after the halogenation step, the drying step may be conducted at a variety of temperatures, pressures, and time periods. While not being limited thereto, the drying step generally may be conducted at a drying temperature in a range from about 15° C. to about 200° C.; alternatively, from about 25° C. to about 150° C.; alternatively, from about 30° C. to about 125° C.; or alternatively, from about 40° C. to about 150° C. In these and other aspects, these temperature ranges also are meant to encompass circumstances where the drying step is conducted at a series of different temperatures, instead of at a single fixed temperature, falling within the respective ranges.

The duration of the drying step is not limited to any particular period of time. Typically, the drying step may be conducted in a drying time ranging from as little as 30 minutes to as long as 36-48 hours (or more), but more typically, the drying step may be conducted in a time period that may be in a range from about 1 hour to about 48 hours, such as, for example, from about 1 hour to about 12 hours, from about 1 hour to about 6 hours, from about 2 hours to about 24 hours, or from about 2 hours to about 6 hours.

The drying pressure employed in the drying step also is not particularly limited. In one aspect, for instance, the drying pressure may be atmospheric pressure, and in such circumstances, the drying temperature may be at least about 30° C., 40° C., or 50° C. In another aspect, the drying pressure may be sub-atmospheric (e.g., vacuum drying), with typical pressures less than or equal to about 100 torr, 80 torr, 60 torr, 40 torr, or 20 torr.

Consistent with aspects of this invention, the drying step may be conducted under conditions sufficient (e.g., time, temperature, pressure) to reduce the solvent content of the halogenated catalyst to less than or equal to about 15 wt. %, less than or equal to about 10 wt. %, or less than or equal to about 8 wt. % solvent. This weight percentage of residual solvent (e.g., water) is based on the weight of the dry halogenated catalyst.

If a calcining step is performed after the halogenation step, the calcining step is often performed after the drying step, and the calcining step may be conducted at a variety of temperatures and time periods. Typical peak calcining temperatures often fall within a range from about 200° C. to about 800° C., such as from about 250° C. to about 600° C., from about 250° C. to about 500° C., or from about 250° C. to about 350° C. In these and other aspects, these temperature ranges also are meant to encompass circumstances where the calcination step is conducted at a series of different temperatures (e.g., an initial calcination temperature, a peak calcination temperature), instead of at a single fixed temperature, falling within the respective ranges. For instance, the calcination step may start at an initial temperature which is the same as the drying temperature in the drying step. Subsequently, the temperature of the calcination may be increased over time to a peak calcining temperature, for example, in a range from about 250° C. to about 500° C.

The duration of the calcining step is not limited to any particular period of time. Hence, the calcining step may be conducted, for example, in a time period ranging from as little as 15-30 minutes to as long as 36-48 hours, or more. The appropriate calcination time may depend upon, for example, the initial/peak calcining temperature and whether a drying step is used, among other variables. Generally, however, the calcining step may be conducted in a time period that may be in a range from about 15 minutes to about 48 hours, such as, for example, from about 15 minutes to about 12 hours, from about 30 minutes to about 24 hours, from about 30 minutes to about 8 hours, or from about 1 hour to about 4 hours.

The calcining step may be conducted in a calcining gas stream that comprises (or consists essentially of, or consists of) an inert gas (e.g., nitrogen), oxygen, air, or any mixture or combination thereof. In some aspects, the calcining gas stream may comprise air, while in other aspects, the calcining gas stream may comprise a mixture of air and nitrogen. Yet, in certain aspects, the calcining gas stream may be an inert gas, such as nitrogen and/or argon.

Depending upon the amount of sulfur contamination and carbon build-up on the sulfur-contaminated catalyst, a carbon burn step (also referred to as a decoking step) may be utilized. If needed, the carbon burn step may be performed prior to the washing step, after the washing step but prior to the halogenation step, or both before the washing step and after the washing step. Generally, in the carbon burn step, the sulfur-contaminated catalyst (or the washed catalyst) may be contacted with a decoking gas stream comprising oxygen. In addition to oxygen, the decoking gas stream may comprise an inert gas, i.e., the decoking gas stream may comprise (or consist essentially of, or consist of) oxygen and an inert gas. Typical inert gasses useful in the carbon burn step may encompass helium, neon, argon, nitrogen, and the like, and this includes combinations of two or more of these materials. In certain aspects, the decoking gas stream may comprise (or consist essentially of, or consist of) oxygen and nitrogen; alternatively, air and nitrogen; or alternatively, air.

Since the decoking gas stream may comprise air, the decoking gas stream may comprise about 20-21 mole % oxygen. More often, however, the amount of oxygen in the decoking gas may be less than about 10 mole %. For example, in some aspects, the decoking gas stream may comprise less than about 8 mole %, less than about 5 mole %, or less than about 3 mole % oxygen. Accordingly, suitable ranges for the mole % of oxygen in the decoking gas stream may include, but are not limited to, the following ranges: from about 0.1 to about 25 mole %, from about 0.1 to about 20 mole %, from about 0.1 to about 10 mole %, from about 0.2 to about 10 mole %, from about 0.2 to about 5 mole %, from about 0.3 to about 5 mole %, from about 0.5 to about 5 mole %, from about 0.5 to about 4 mole %, from about 0.5 to about 3 mole %, or from about 1 to about 3 mole %, and the like.

In an aspect, the decoking gas stream may be substantially halogen-free, i.e., substantially free of halogen-containing compounds. In this context, "substantially halogen-free" means less than 100 ppmw (ppm by weight) of halogen-containing compounds, such as chlorine-containing compounds, in the decoking gas stream. Therefore, it is contemplated that the amount of halogen-containing compounds in the decoking gas stream may be less than 50 ppmw, less than 40 ppmw, less than 25 ppmw, less than 10 ppmw, less than 5 ppmw, or less than 3 ppmw, in certain aspects. In other aspects, the amount of halogen-containing compounds in the decoking gas stream may be in range from about 0.1 to about 100 ppmw, from about 0.5 to about 100 ppmw, from about 1 to about 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, it is believed that it may be beneficial to have substantially no halogens, such as chlorine, added during the carbon burn step of the method of regenerating a sulfur-contaminated catalyst.

In another aspect, the decoking gas stream may be substantially free of water, and in this regard, "substantially free" means less than 100 ppmw (ppm by weight) of water in the decoking gas stream. Therefore, it is contemplated that the amount of water in the decoking gas stream may be less than 50 ppmw, less than 25 ppmw, less than 10 ppmw, less than 5 ppmw, or less than 3 ppmw, in certain aspects. In other aspects, the amount of water in the decoking gas stream may be in range from about 0.1 to about 100 ppmw, from about 0.5 to about 100 ppmw, from about 1 to about 100 ppmw, from about 0.1 to about 50 ppmw, from about 0.1 to about 25 ppmw, from about 0.1 to about 10 ppmw, or from about 0.1 to about 5 ppmw. While not wishing to be bound by theory, it is believed that it may be beneficial to have substantially no water added during the carbon burn step of the method of regenerating a sulfur-contaminated catalyst.

Similar to that described above for the aqueous solution and the halogen solution, any compositional attributes of the decoking gas stream are meant to refer to the incoming decoking gas stream, prior to contacting the catalyst (sulfur-contaminated catalyst, washed catalyst), unless expressly stated otherwise. As one of skill in the art would readily recognize, the outgoing decoking gas stream, after contacting the catalyst, may vary significantly in composition from the incoming decoking gas stream. For instance, chlorine may elute, in some circumstances, from the catalyst during the carbon burn step. Moreover, water may be produced during the carbon burn step, and thus, water may be detected in the outgoing decoking stream.

The carbon burn step may be conducted at a variety of temperatures and time periods. For instance, the carbon burn step may be conducted at a peak decoking temperature in a range from about 150° C. to about 600° C.; alternatively, from about 200° C. to about 500° C.; alternatively, from about 300° C. to about 600° C.; alternatively, from about 300° C. to about 550° C.; alternatively, from about 300° C. to about 500° C.; alternatively, from about 320° C. to about 480° C.; alternatively, from about 340° C. to about 460° C.; or alternatively, from about 350° C. to about 450° C. In these and other aspects, these temperature ranges also are meant to encompass circumstances where the carbon burn step is conducted at a series of different temperatures (e.g., an initial decoking temperature, a peak decoking temperature), instead of at a single fixed temperature, falling within the respective ranges. For instance, and not limited thereto, the carbon burn step may commence at an initial decoking temperature in a range from about 0° C. to about 300° C., from about 20° C. to about 250° C., from about 50° C. to about 200° C., or from about 150° C. to about 260° C. Subsequently, the temperature of the carbon burn step may be increased to a peak decoking temperature, for example, in a range from about 300° C. to about 600° C., or from about 350° C. to about 450° C.

The duration of the carbon burn step is not limited to any particular period of time. Hence, the carbon burn step may be conducted, for example, in a time period ranging from as little as 30-45 minutes to as long as 48-72 hours, or more. The appropriate decoking time may depend upon, for example, the initial/peak decoking temperature and the amount of oxygen in the decoking gas stream, among other variables. Generally, however, the carbon burn step may be conducted in a time period that may be in a range from about 45 minutes to about 72 hours, such as, for example, from about 1 hour to about 72 hours, from about 24 hours to about 72 hours, from about 12 hours to about 60 hours, from about 12 hours to about 48 hours, or from about 1 hour to about 6 hours.

Alternatively, the carbon burn step may be conducted for a time period sufficient to reduce the wt. % of carbon on the catalyst, after the carbon burn step, to less than about 5 wt. %, or less than about 1 wt. % (a de-coked catalyst). In some aspects, the carbon burn step may be conducted for a time period sufficient to reduce the wt. % of carbon on the catalyst to within a range from about 0.01 wt. % to about 1.5 wt. %, from about 0.01 wt. % to about 1 wt. %, from about 0.1 wt. % to about 1 wt. %, from about 0.1 wt. % to about 0.75 wt. %, from about 0.25 wt. % to about 1.5 wt. %, or from about 0.25 wt. % to about 1 wt. %. In other aspects, the carbon burn step may be conducted for a time period determined by monitoring the $CO_2$ level in the outgoing or exiting decoking stream, after contacting the catalyst. Hence, the carbon burn step may be conducted for a time period sufficient to reduce the amount of $CO_2$ in the outgoing or exiting decoking stream, after contacting the catalyst, to less than about 100 ppmv, for example, less than about 50 ppmv, or less than about 20 ppmv. In various aspects contemplated herein, the methods of regenerating a sulfur-contaminated catalyst may further include a hydrocarbon removal step performed prior to the washing step (and the carbon burn step, if utilized). The hydrocarbon removal step generally may comprise contacting the sulfur-contaminated catalyst with a hydrocarbon removal gas stream comprising oxygen.

The composition of the hydrocarbon removal gas stream may encompass the same potential attributes as that described above for the decoking gas stream employed in the carbon burn step. Thus, in addition to oxygen, the hydrocarbon removal gas stream may comprise an inert gas, such as helium, neon, argon, and/or nitrogen. In an aspect, the hydrocarbon removal gas stream may comprise (or consist essentially of, or consist of) oxygen and nitrogen; alternatively, air and nitrogen; or alternatively, air. In another aspect, the hydrocarbon removal gas stream often may comprise, for example, from about 0.1 to about 25 mole % oxygen, from about 0.1 to about 20 mole % oxygen, from about 0.2 to about 10 mole % oxygen, from about 0.2 to about 5 mole % oxygen, from about 0.3 to about 5 mole % oxygen, from about 0.5 to about 5 mole % oxygen, from about 0.5 to about 4 mole % oxygen, from about 0.5 to about 3 mole % oxygen, or from about 1 to about 3 mole % oxygen, and the like. In yet another aspect, the hydrocarbon removal gas stream may be substantially halogen-free or substantially free of halogen-containing compounds, i.e., having less than 100 ppmw (ppm by weight) of halogen-containing compounds in the hydrocarbon removal gas stream, such as, for example, less than 50 ppmw, less than 25 ppmw, less than 10 ppmw, less than 5 ppmw, or less than 3 ppmw, of halogen-containing compounds in the hydrocarbon removal gas stream. In still another aspect, the hydrocarbon removal gas stream may be substantially free of water, i.e., having less than 100 ppmw of water in the hydrocarbon removal gas stream, such as, for example, less than 50 ppmw, less than 25 ppmw, less than 10 ppmw, less than 5 ppmw, or less than 3 ppmw, of water in the hydrocarbon removal gas stream. As above, any compositional attributes of the hydrocarbon removal gas stream are meant to refer to the incoming hydrocarbon removal gas stream, prior to contacting the sulfur-contaminated catalyst, unless expressly stated otherwise.

The hydrocarbon removal step differs from the carbon burn step in that it may be conducted at a much lower temperature. Generally, the hydrocarbon removal step may be conducted at a hydrocarbon removal temperature in a range from about 125° C. to about 350° C.; alternatively, from about 125° C. to about 300° C.; alternatively, from about 150° C. to about 250° C.; alternatively, from about 175° C. to about 350° C.; alternatively, from about 150° C. to about 225° C.; or alternatively, from about 175° C. to about 300° C. In these and other aspects, these temperature ranges also are meant to encompass circumstances where the hydrocarbon removal step is conducted at a series of different temperatures, instead of at a single fixed temperature, falling within the respective ranges.

The duration of the hydrocarbon removal step is not limited to any particular period of time. Typically, the hydrocarbon removal step may be conducted in a time period ranging from as little as 30-45 minutes to as long as 48 hours (or more), but more typically, the hydrocarbon removal step may be conducted in a time period that may be in a range from about 1 hour to about 36 hours, such as, for example, from about 2 hours to about 36 hours, from about 1 hour to about 24 hours, from about 1 hour to about 18 hours, or from about 2 hours to about 24 hours.

Alternatively, the hydrocarbon removal step may be conducted for a time period sufficient to reduce the wt. % of hydrocarbons on the sulfur-contaminated catalyst to within a range from about 1 wt. % to about 10 wt. %, such as, for example, from about 2 wt. % to about 10 wt. %, from about 2 wt. % to about 8 wt. %, from about 1 wt. % to about 7 wt. %, from about 1 wt. to about 5 wt. %, or from about 2 wt. to about 6 wt. % carbon. While not wishing to be bound by theory, it is believed that operational health and safety benefits may be achieved by removing liquid hydrocarbons and light oligomers prior to opening an aromatization reactor, or storing or shipping the sulfur-contaminated catalyst for off-site regeneration.

The methods of regenerating a sulfur-contaminated catalyst disclosed herein may further comprise a reducing step after the halogenation step, thereby forming a reactivated catalyst. This reducing step may comprise contacting the regenerated catalyst (e.g., the halogenated catalyst) with a reducing gas stream comprising molecular hydrogen. In addition to molecular hydrogen, the reducing gas stream may comprise an inert gas, i.e., the reducing gas stream may comprise (or consist essentially of, or consist of) molecular hydrogen and an inert gas. Typical inert gasses useful in the reducing step may encompass helium, neon, argon, nitrogen, and the like, and this includes combinations of two or more of these materials. In certain aspects, the reducing gas stream may comprise (or consist essentially of, or consist of) molecular hydrogen and nitrogen. This reducing step may be performed in the aromatization reactor system prior to commencing reforming operations.

In some aspects, molecular hydrogen may be the major component of the reducing gas stream, while in other aspects, molecular hydrogen may be a minor component. For example, the reducing gas stream may comprise at least about 25 mole % molecular hydrogen, at least about 35 mole % molecular hydrogen, at least about 50 mole % molecular hydrogen, at least about 65 mole % molecular hydrogen, at least about 75 mole % molecular hydrogen, or 100 mole % molecular hydrogen. Accordingly, suitable ranges for the mole % of molecular hydrogen in the reducing gas stream may include, but are not limited to, the following ranges: from about 25 to 100 mole %, from about 50 to 100 mole %, from about 25 to 100 mole %, from about 35 to 100 mole %, from about 55 to 100 mole %, from about 25 to about 75 mole %, from about 35 to about 65 mole %, or from about 70 to 100 mole %, and the like.

The reducing step may be conducted at a variety of temperatures and time periods. For instance, the reducing step may be conducted at a peak reducing temperature in a range from about 200° C. to about 600° C.; alternatively, from about 300° C. to about 550° C.; alternatively, from about 400° C. to about 600° C.; alternatively, from about 350° C. to about 575° C.; alternatively, from about 400° C. to about 550° C.; or alternatively, from about 450° C. to about 550° C. In these and other aspects, these temperature ranges also are meant to encompass circumstances where the reducing step is conducted at a series of different temperatures (e.g., an initial reducing temperature, a peak reducing temperature), instead of at a single fixed temperature, falling within the respective ranges.

The duration of the reducing step is not limited to any particular period of time. Hence, the reducing step may be conducted, for example, in a time period ranging from as little as 1 hour to as long as 48-72 hours, or more. For example, the reducing step may be conducted in a time period that may be in a range from about 2 hours to about 48 hours, from about 3 hours to about 36 hours, from about 5 hours to about 36 hours, from about 2 hours to about 30 hours, or from about 10 hours to about 30 hours.

As described herein, the "regenerated" catalyst may be, for instance, (a) a sulfur-contaminated catalyst that has been subjected to a washing step and a halogenation step (a halogenated catalyst); (b) a sulfur-contaminated catalyst that has been subjected to a washing step, a halogenation step, a drying step, and a calcining step; or (c) a sulfur-contaminated catalyst that has been subjected to a carbon burn step, a washing step, a halogenation step, a drying step, and a calcining step. Moreover, this includes catalysts that also have been subjected to a drying step and/or a calcining step between washing and halogenation. Further, as described herein, the "reactivated" catalyst is the regenerated catalyst that has been subjected to a reducing step. The regenerated catalysts and reactivated catalysts produced in accordance with the disclosed methods often may be characterized by one or more of the following features, and in any combination.

Regenerated catalysts and reactivated catalysts produced by the methods disclosed herein often have much less sulfur than that present in the sulfur-contaminated catalyst, for instance, at least about 20% less, at least about 25% less, or at least about 35%, and often up to about 70%, 80%, or 90% less. In some aspects, the regenerated catalyst or reactivated catalyst may contain less than about 400 ppmw, less than about 200 ppmw, or less than about 150 ppmw sulfur. Illustrative and non-limiting ranges include from about 25 ppmw to about 400 ppmw, from about 70 ppmw to about 200 ppmw, or from about 50 ppmw to about 150 ppmw sulfur, based on the weight of the regenerated catalyst or reactivated catalyst. As described herein, these amounts of sulfur are based on the respective "dry" catalyst.

Regenerated catalysts or reactivated catalysts also may have various levels of carbon, including but not limited to the following representative ranges: from about 0.01 wt. % to about 5 wt. %, from about 0.1 wt. % to about 1 wt. %, from about 0.25 to about 1 wt. %, or from about 0.25 wt. % to about 0.5 wt. % carbon. Generally, the methods disclosed herein typically result in regenerated catalysts or reactivated catalysts containing from about 0.01 wt. % to about 10 wt. %, from about 0.1 wt. % to about 10 wt. %, from about 0.5 wt. % to about 5 wt. %, or from about 0.5 wt. % to about 2 wt. % chlorine. Likewise, the methods disclosed herein typically result in regenerated catalysts or reactivated catalysts containing from about 0.01 wt. % to about 10 wt. %, from about 0.1 wt. % to about 10 wt. %, from about 0.5 wt. % to about 5 wt. %, or from about 0.5 wt. % to about 2 wt. % fluorine. Additionally or alternatively, the regenerated catalyst or reactivated catalyst may contain less than about 0.1 wt. % of barium, less than about 0.01 wt. % barium, or no barium (no measurable amount). Additionally or alternatively, the regenerated catalyst or reactivated catalyst may contain from about 0.5 wt. % to about 15 wt. % alkali metal, from about 1 wt. % to about 14 wt. % alkali metal, or from about 2 wt. % to about 13 wt. % alkali metal. These weight percentages are based on the weight of the respective "dry" catalyst.

Consistent with the methods of this invention, the surface area of the regenerated catalyst or reactivated catalyst generally may be maintained. For instance, the surface area of the regenerated catalyst or reactivated catalyst may be at least about 40%, at least about 50%, at least about 60%, and often up to about 70%, 80%, or more, of the surface area of the sulfur-contaminated catalyst.

Reforming Methods with Aromatization Catalysts

Also encompassed herein are various methods for reforming hydrocarbons. One such reforming method may comprise (or consist essentially of, or consist of):

(A) contacting a hydrocarbon feed with an aromatization catalyst comprising a transition metal and a catalyst support under reforming conditions in a reactor system to produce an aromatic product;

(B) contacting a sulfur-contaminated hydrocarbon feed with the aromatization catalyst for a time period sufficient to form a sulfur-contaminated catalyst;

(C) washing the sulfur-contaminated catalyst with an aqueous solution to produce a washed catalyst, the aqueous solution optionally comprising an alkali metal; and (D) contacting the washed catalyst with a halogen solution comprising chlorine, fluorine, or mixtures thereof, to produce a halogenated catalyst.

Generally, the features of any of the reforming methods disclosed herein (e.g., the hydrocarbon feed, the aromatization catalyst, the transition metal, the catalyst support, the reforming conditions, the aqueous solution, the halogen solution, the conditions under which the washing step is conducted, and the conditions under which the halogenation step is conducted, among others) are independently described herein, and these features may be combined in any combination to further describe the disclosed reforming methods. Moreover, other process steps may be conducted before, during, and/or after any of the steps listed in the disclosed reforming methods, unless stated otherwise.

The washing step (step (C)) and the halogenation step (step (D)) are discussed hereinabove. Any aspects and features of the washing step and/or the halogenation step (as well as other steps that may be conducted before, during and/or after the washing step and/or the halogenation step) described herein may be utilized in the methods for reforming hydrocarbons and, accordingly, are encompassed herein.

In these reforming methods, step (A) may comprise contacting a hydrocarbon feed with an aromatization catalyst under reforming conditions in a reactor system to produce an aromatic product. The reactor systems for reforming and the respective reforming conditions are well known to those of skill in the art and are described, for example, in U.S. Pat. Nos. 4,456,527, 5,389,235, 5,401,386, 5,401,365, 6,207,042, and 7,932,425, the disclosures of which are incorporated herein by reference in their entirety.

Likewise, typical hydrocarbon feeds are disclosed in these references. Often, the hydrocarbon feed may be a naphtha stream or light naphtha stream. In certain aspects, the hydrocarbon feed may comprise $C_6$-$C_8$ alkanes and/or cycloalkanes (e.g., hexane, heptane, and cyclohexane).

Step (B) in the reforming methods indicates that a sulfur-contaminated hydrocarbon feed may be contacted with the aromatization catalyst for a time period sufficient for the aromatization catalyst to become sulfur-contaminated catalyst. This sulfur-contaminated catalyst typically will have unacceptable performance in one or more of catalyst activity, hydrocarbon feed conversion, yield to a desired product(s), selectivity to a desired product(s), or an operating parameter, such as output/production rate or reforming temperature, although not limited thereto. Once the aromatization catalyst is contaminated with sulfur, the regeneration steps (C) and (D), amongst others, may be performed.

In an aspect, the method of reforming may be an in situ process, for example, steps (A)-(D) may be performed in the same reactor system. However, in an alternative aspect, one or more of the catalyst regeneration steps (C)-(D) may be conducted external to the reforming reactor system, such as in another vessel and/or location. For instance, washing step (C), or halogenation step (D), or both washing step (C) and halogenation step (D), may be performed externally to the reactor system used in steps (A)-(B).

In another aspect, the reforming process may further comprise a step of reactivating the catalyst after step (D). This may be accomplished with a reducing step, as described hereinabove. Any catalyst regenerated or any catalyst reactivated by any of the processes described herein is considered within the scope of this disclosure and encompassed herein. In some aspects, the regenerated catalyst or reactivated catalyst may have from about 50% to about 90% of the catalyst activity of fresh aromatization catalyst of the same production run of catalyst, tested on the same equipment, and under the same method and test conditions.

Transition Metal Based Catalysts

The methods and techniques disclosed herein may be utilized with any suitable aromatization catalyst. The aromatization catalyst (fresh, sulfur-contaminated, regenerated, or reactivated) generally may comprise a transition metal and a catalyst support. The catalyst support typically may comprise an inorganic oxide bound with a support matrix (or binder), examples of the inorganic oxide may include, but are not limited to, medium and/or large pore zeolites (aluminosilicates), amorphous inorganic oxides, as well as mixtures thereof. Large pore zeolites often may have average pore diameters in a range of from about 7 Å to about 12 Å, and non-limiting examples of large pore zeolites include L-zeolite, Y-zeolite, mordenite, omega zeolite, beta zeolite, and the like. Medium pore zeolites often may have average pore diameters in a range of from about 5 Å to about 7 Å. A catalyst support having a medium and/or large pore zeolites bound with a support matrix may be referred to herein as a "zeolitic support." Amorphous inorganic oxides may include, but are not limited to, aluminum oxide, silicon oxide, titania, and combinations thereof.

The term "zeolite" generally refers to a particular group of hydrated, crystalline metal aluminosilicates. These zeolites exhibit a network of $SiO_4$ and $AlO_4$ tetrahedra in which aluminum and silicon atoms are crosslinked in a three-dimensional framework by sharing oxygen atoms. In the framework, the ratio of oxygen atoms to the total of aluminum and silicon atoms may be equal to 2. The framework exhibits a negative electrovalence that typically may be balanced by the inclusion of cations within the crystal, such as metals, alkali metals, alkaline earth metals, and/or hydrogen.

In some aspects, the catalyst support may comprise an L-type zeolite. Catalyst supports comprising L-type zeolite are zeolitic supports. L-type zeolites may contain mole ratios of oxides in accordance with the formula: $M_{2/n}OAl_2O_3xSiO_2yH_2O$. In this formula, "M" designates an exchangeable cation (one or more) such as barium, calcium, cerium, lithium, magnesium, potassium, sodium, strontium, cesium, and/or zinc, as well as non-metallic cations like hydronium and ammonium ions, which may be replaced by other exchangeable cations without causing a substantial alteration of the basic crystal structure of the L-type zeolite. The "n" in the formula represents the valence of "M"; "x" is 2 or greater; and "y" is the number of water molecules contained in the channels or interconnected voids of the zeolite.

In one aspect, the catalyst support may comprise a bound potassium L-type zeolite, also referred to as a KL-zeolite, while in another aspect, the catalyst support may comprise a barium ion-exchanged L-zeolite. As used herein, the term "KL-zeolite" refers to L-type zeolites in which the principal cation M incorporated in the zeolite is potassium. A KL-zeolite may be cation-exchanged (e.g., with barium) or impregnated with a transition metal and one or more halides to produce a transition metal impregnated, halided zeolite or a KL supported transition metal-halide zeolite catalyst.

In the catalyst support the zeolite may be bound with a support matrix (or binder), non-limiting examples of which may include silica, alumina, magnesia, boria, titania, zirconia, various clays, and the like, including mixed oxides thereof, as well as mixtures thereof. For example, the catalyst support may comprise a support matrix comprising alumina, silica, a mixed oxide thereof, or a mixture thereof. The zeolite may be bound with the support matrix using any method known in the art.

The aromatization catalyst may comprise a transition metal, and non-limiting examples of suitable transition metals may include iron, cobalt, nickel, ruthenium, rhodium, rhenium, palladium, osmium, iridium, platinum, gold, silver, copper, and the like, or a combination of two or more transition metals. In one aspect, the transition metal may comprise a Group 8-11 transition metal, a Group 10-11 transition metal (one or more), or a Group 10 transition metal, while in another aspect, the transition metal may comprise platinum (Pt).

In one aspect, the catalyst (fresh, sulfur-contaminated, regenerated, or reactivated) may comprise from about 0.1 wt. % to about 10 wt. % transition metal. In another aspect, the catalyst may comprise from about 0.3 wt. % to about 5 wt. % transition metal. In yet another aspect, the catalyst may comprise from about 0.3 wt. % to about 3 wt. % transition metal, or from about 0.5 wt. % to about 2 wt. % transition metal. These weight percentages are based on the weight of the respective "dry" catalyst.

In circumstances where the transition metal comprises platinum, the catalyst (fresh, sulfur-contaminated, regenerated, or reactivated) may comprise from about 0.1 wt. % to about 10 wt. % platinum; alternatively, from about 0.3 wt. % to about 5 wt. % platinum; alternatively, from about 0.3 wt. % to about 3 wt. % platinum; or alternatively, from about 0.5 wt. % to about 2 wt. % platinum. In a particular aspect contemplated herein, the aromatization catalyst may comprise platinum and a zeolitic support comprising a KL-zeolite.

While not being limited thereto, the catalyst (fresh, sulfur-contaminated, regenerated, or reactivated) may comprise from about 5 wt. % to about 35 wt. % support matrix. For example, the catalyst may comprise from about 5 wt. % to about 30 wt. %, or from about 10 wt. % to about 30 wt. % support matrix. Similar to above, these weight percentages are based on the weight of the respective dry catalyst.

Examples of representative and non-limiting catalysts that are encompassed herein include those disclosed in U.S. Pat. Nos. 5,196,631, 6,190,539, 6,406,614, 6,518,470, 6,812,180, and 7,153,801, the disclosures of which are incorporated herein by reference in their entirety.

As disclosed herein, the catalyst (fresh, sulfur-contaminated, regenerated, or reactivated) may comprise a halogen, such as chlorine, fluorine, bromine, iodine, or a combination of two or more halogens. For example, the catalyst may contain both chlorine and fluorine, independently, at an amount of from greater than 0 wt. % to about 5 wt. %, from about 0.05 wt. % to about 2 wt. %, or from about 0.1 wt. % to about 1 wt. %. In certain aspects, the molar ratio of chlorine:fluorine may be in the range of from about 0.5:1 to about 4:1. Other suitable molar ratios of Cl:F may include the following non-limiting ranges: from about 1:1 to about 4:1, from about 0.5:1 to about 3:1, from about 1:1 to about 3:1, from about 0.5:1 to about 2:1, or from about 1:1 to about 2.5:1.

In particular aspects of this invention, the catalyst (fresh, sulfur-contaminated, regenerated, or reactivated) may be substantially free of barium, often containing less than about 0.1 wt. % of barium. In some aspects, the catalyst may contain less than about 0.01 wt. % barium, or may contain no barium (no measurable amount of barium).

Also encompassed herein are regenerated catalysts or reactivated catalysts produced by any of the methods described herein. In an aspect, the reactivated catalyst or regenerated catalyst may comprise any suitable amount of an alkali metal, typically ranging from about 0.5 wt. % to about 15 wt. % alkali metal; alternatively, from about 1 wt. % to about 14 wt. % alkali metal; or alternatively, from about 2 wt. % to about 13 wt. % alkali metal, based on the weight of the dry reactivated or regenerated catalyst.

The methods provided herein are very effective at restoring catalytic activity to an aromatization catalyst that has been contaminated with sulfur. For instance, and beneficially, the reactivated catalyst or regenerated catalyst may be characterized by a TEOR (end of run temperature) within about 70° F., within about 60° F., within about 55° F., or within about 50° F., of the TEOR of a fresh reference catalyst (from the same production run (or batch) of catalyst, tested on the same equipment, and under the same test method and conditions). Additionally or alternatively, the reactivated catalyst or regenerated catalyst may be characterized by a TSOR (start of run temperature) within about 55° F., within about 50° F., within about 45° F., or within about 40° F., of the TSOR of a fresh reference catalyst (from the same production run (or batch) of catalyst, tested on the same equipment, and under the same test method and conditions).

Moreover, the reactivated catalyst or regenerated catalyst may be characterized by relatively low fouling rates, as described herein. The reactivated catalyst or regenerated catalyst may have a fouling rate (FR, slope of temperature versus time) ranging from about 0.05° F./hr to about 0.6° F./hr, from about 0.05° F./hr to about 0.5° F./hr, from about 0.1° F./hr to about 0.5° F./hr, or from about 0.15° F./hr to about 0.45° F./hr.

The reactivated catalyst or regenerated catalyst also may be characterized by its platinum dispersion. In some aspects, the platinum dispersion may be in a range from about 20% to about 50%, or from about 25% to about 55%.

In addition to these beneficial features, the methods provided herein also are very effective at restoring catalytic selectivity to an aromatization catalyst that has been contaminated with sulfur. For instance, and beneficially, the reactivated catalyst or regenerated catalyst may be characterized by an aromatics selectivity in range from about 0.88 to about 0.94, or from about 0.89 to about 0.94. In some instances, and unexpectedly, the aromatics selectivity may be greater than or within about 2 percent of the selectivity of the fresh reference catalyst.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

Catalysts were tested for their respective fouling rates (abbreviated FR, units of °F./hr), which correlate to their activities by the formula, y=FR*t+TSOR, where y is temperature, FR is the fouling rate, t is time, and TSOR is the initial Start of Run temperature. The FR of a catalyst sample was determined by plotting the temperature (yield adjusted catalyst temperature) required to maintain a total yield of aromatics (such as benzene and toluene) at 63 wt. % over time at standard test conditions, as described later herein. The FR's were then determined from the calculated slopes fit to the resulting data using linear regression. The total time on stream was 40 hours, and the End of Run temperature (abbreviated TEOR) at 40 hours also was determined. In order to exclude the catalyst break-in period, only data from 15+ hours online was included in the TSOR and FR calculations.

In each of the examples, the following standard testing procedures were utilized. The catalysts were ground and sieved to 25-45 mesh and 0.69 g (~1 cc) of the sieved catalyst was placed in a ⅜-inch OD stainless steel reactor vessel in a temperature controlled furnace. After reducing the catalyst under flowing molecular hydrogen, a feed stream of aliphatic hydrocarbons (12 mL/min) and molecular hydrogen (43 mL/min) was introduced to the reactor vessel at a pressure of 100 psig, a $H_2$:hydrocarbon molar ratio of 1.3, and a liquid hourly space velocity (LHSV) of 12 $hr^{-1}$ to obtain catalyst performance data over time. The hydrocarbon feed contained from 22 to 26 wt. % n-hexane, 4 to 8 wt. % n-heptane, 33 to 37 wt. % $C_6$ iso-paraffins, 15 to 21 wt. % $C_7$ iso-paraffins, 6 to 10 wt. % $C_8$ iso-paraffins, with the balance attributable to $C_6$ olefins, naphthenes, $C_5$-species, and aromatics. The reactor effluent composition was analyzed by gas chromatography (using a capillary column and a flame ionization detector) to determine the amount of aromatics, such as benzene and toluene.

Sulfur content was measured by inductively coupled plasma spectroscopy (ICP). Surface areas were determined using the BET method, and micropore volumes were determined using the t-plot method. Platinum dispersion was determined by CO chemisorption.

In Examples 1-5, experiments were conducted to demonstrate the effectiveness of various processes and steps in regenerating a sulfur-contaminated aromatization catalyst, with the performance of a fresh aromatization catalyst used as a target baseline. The fresh aromatization catalyst (Example 1) was a Pt/KL-zeolite containing approximately 1 wt. % platinum, 0.7-0.9 wt. % Cl and 0.7-0.9 wt. % F, and having a surface area of approximately 178 $m^2$/g and a micropore volume of 0.062 cc/g. The source of the sulfur-contaminated catalyst (Example 2) was the fresh catalyst, but after it had been deactivated after contact with sulfur. Prior to usage in these examples, the sulfur-contaminated aromatization catalyst was subjected to a hydrocarbon removal treatment to remove unreacted hydrocarbons and some carbonaceous deposits from the sulfur-contaminated catalyst.

For the treatment procedure in Example 3, 1.43 g of ammonium chloride and 1.82 g of ammonium fluoride were dissolved into 35 mL of deionized water. Next, 100 g of the sulfur-contaminated catalyst of Example 2 were impregnated with the halogen solution. The impregnated material was allowed to soak for 4 hours at room temperature. It was then dried at 43 torr and 38° C. for 2 hours. The temperature was then increased to 95° C. for 1 hour. Lastly, the catalyst was calcined in flowing air at 900° F. for 1 hour.

For the treatment procedure in Example 4, 100 g of the sulfur-contaminated catalyst of Example 2 were first washed with deionized water. The washing conditions consisted of 3 wash cycles, each conducted at 100° F. for 20 minutes with the weight of the wash water being 2.5 times the weight of the catalyst. The washing was performed batchwise with $N_2$ bubbling to agitate the mixture. The washed catalyst was next dried at 250° F. for 4 hours and calcined at 900° F. for 1 hour under air flow. Halogenation, drying, and calcining were performed in the same manner as in Example 3.

For the treatment procedure in Example 5, 100 g of the sulfur-contaminated catalyst of Example 2 were washed with deionized water containing KCl (0.1 M). The washing conditions consisted of 3 wash cycles, each conducted at 100° F. for 20 minutes with the weight of the wash water (excluding KCl) being 2.5 times the weight of the catalyst. The washing was performed batchwise with $N_2$ bubbling to agitate the mixture. The washed catalyst was next dried at 250° F. for 4 hours and calcined at 900° F. for 1 hour under air flow. Halogenation, drying, and calcining were performed in the same manner as in Example 3.

Figure 2:
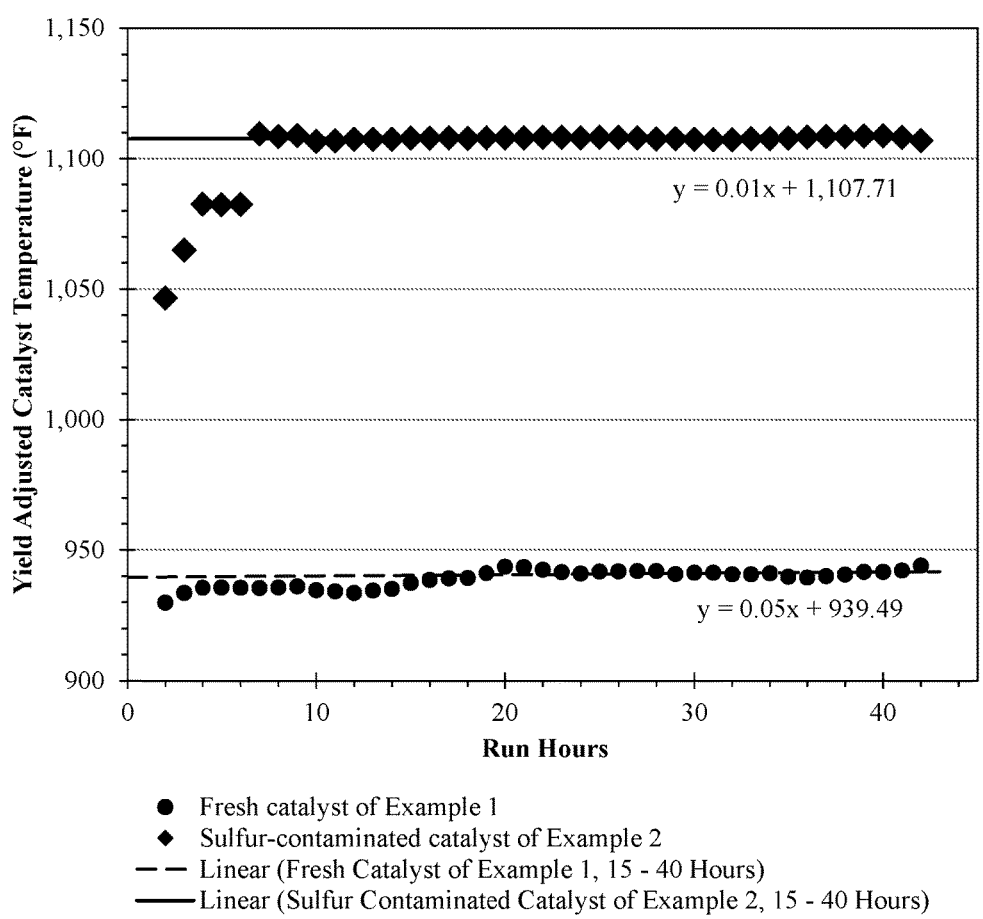
FIG. 2 presents a plot of the yield adjusted temperature versus reaction time for the fresh catalyst of Example 1 and the sulfur-contaminated catalyst of Example 2.
Figure 3:
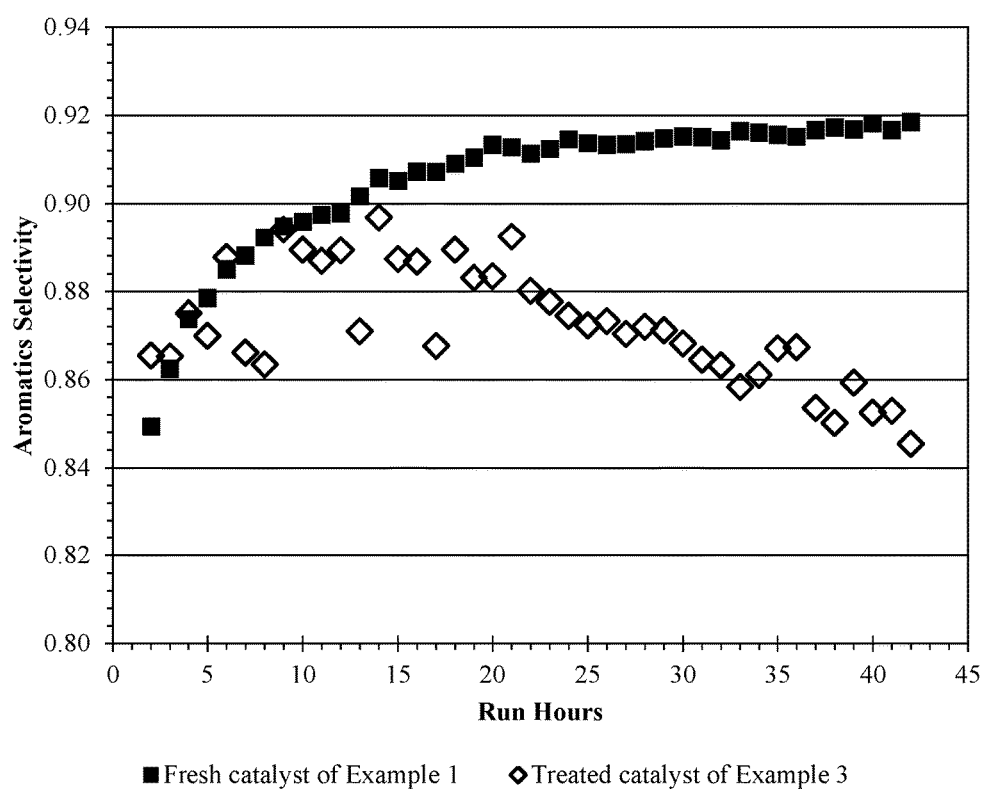
FIG. 3 presents a plot of the aromatics selectivity versus reaction time for the fresh catalyst of Example 1 and the treated catalyst of Example 3, in which no washing step was used.
Figure 4:
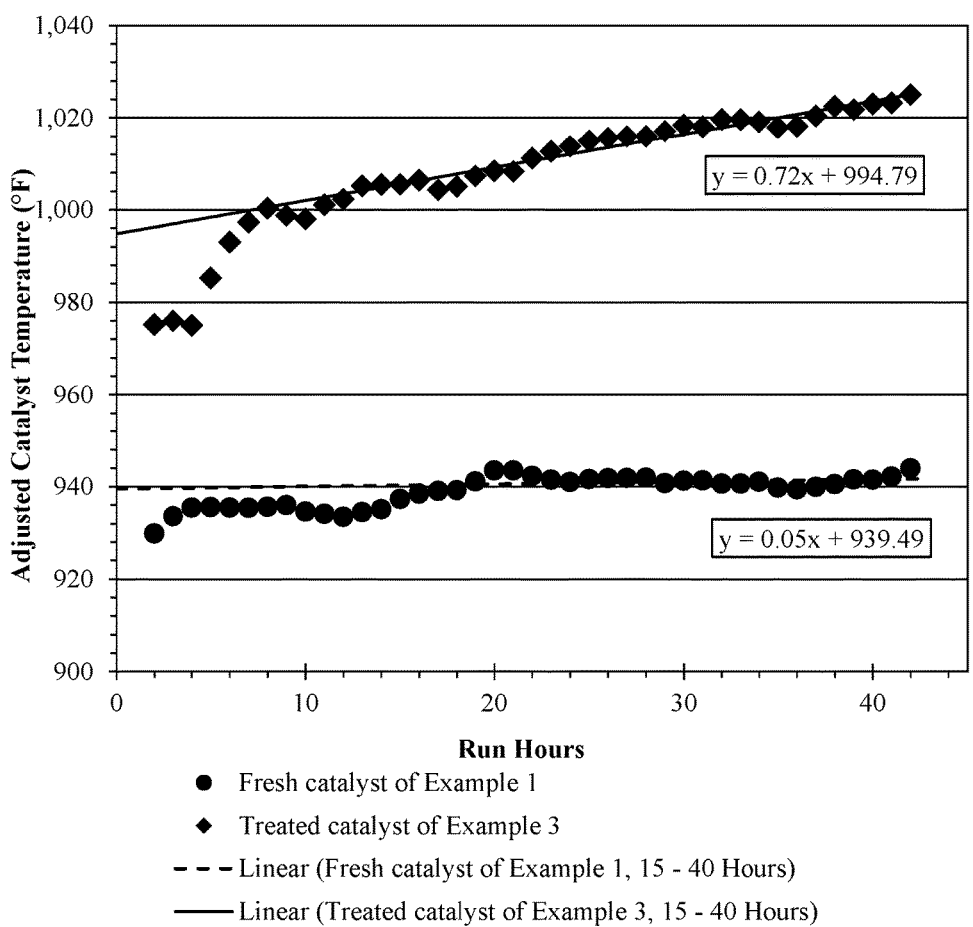
FIG. 4 presents a plot of the yield adjusted temperature versus reaction time for the fresh catalyst of Example 1 and the treated catalyst of Example 3, in which no washing step was used.
Figure 5:
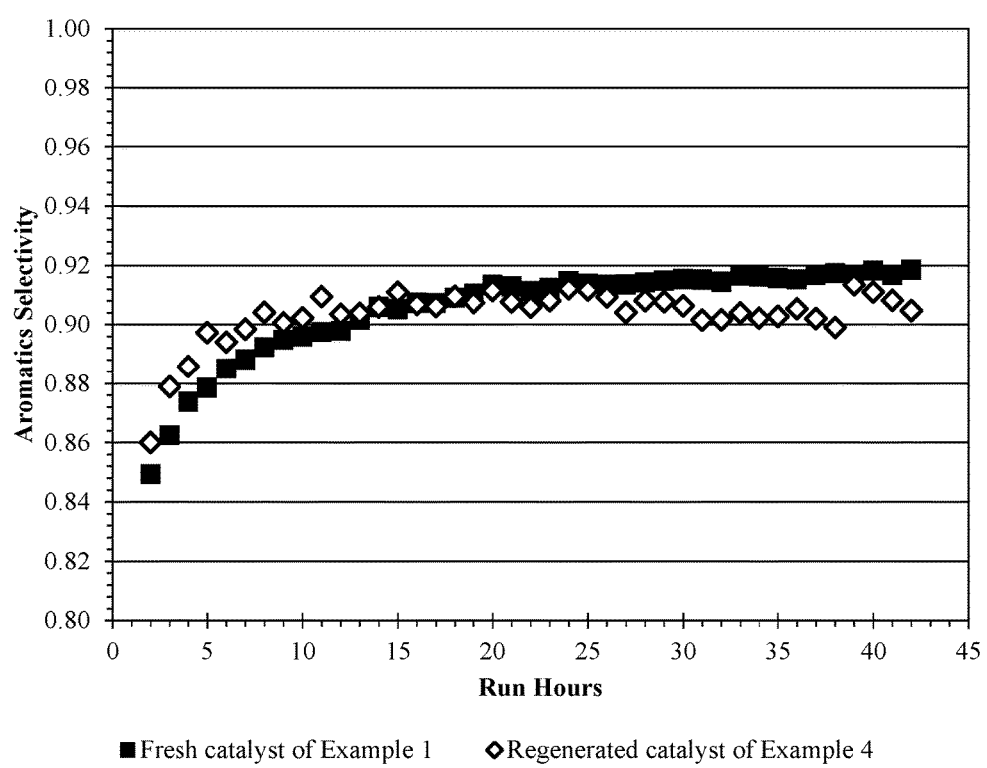
FIG. 5 presents a plot of the aromatics selectivity versus reaction time for the fresh catalyst of Example 1 and the regenerated catalyst of Example 4, in which the sulfur-contaminated catalyst was subjected to a water washing step and a halogenation step.
Figure 6:
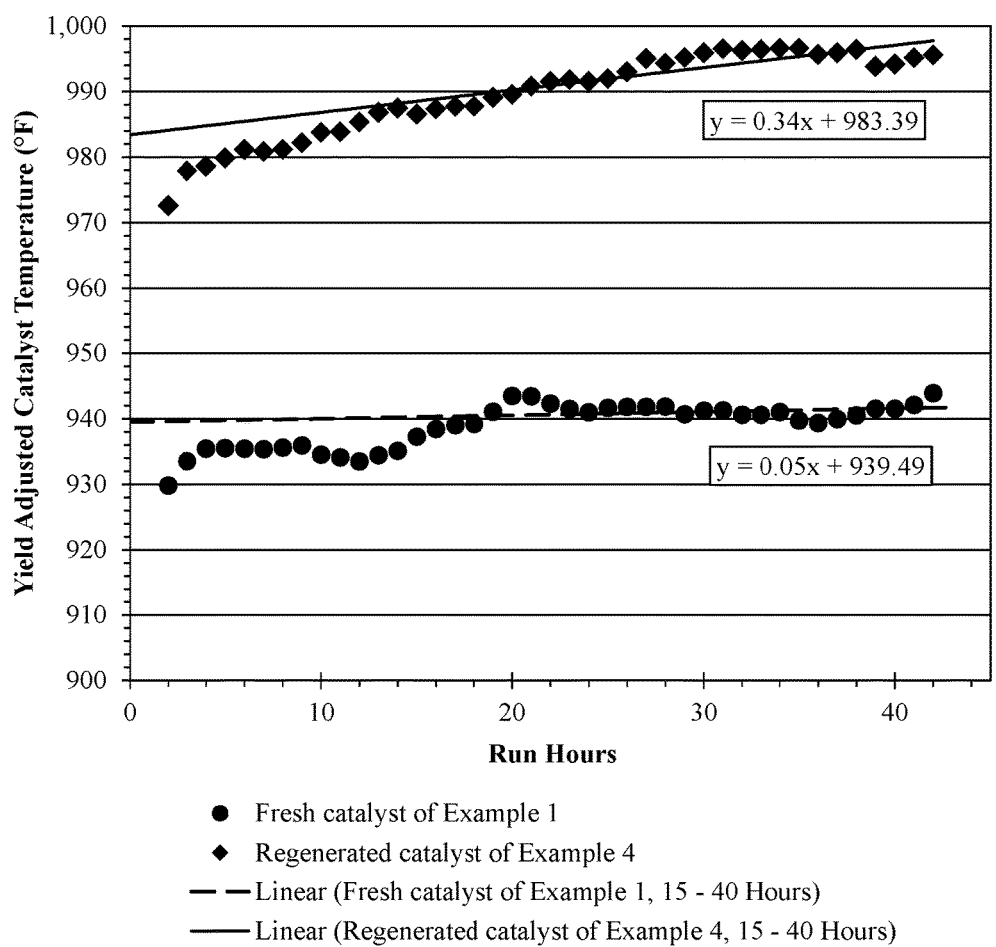
FIG. 6 presents a plot of the yield adjusted temperature versus reaction time for the fresh catalyst of Example 1 and the regenerated catalyst of Example 4, in which the sulfur-contaminated catalyst was subjected to a water washing step and a halogenation step.
Figure 7:
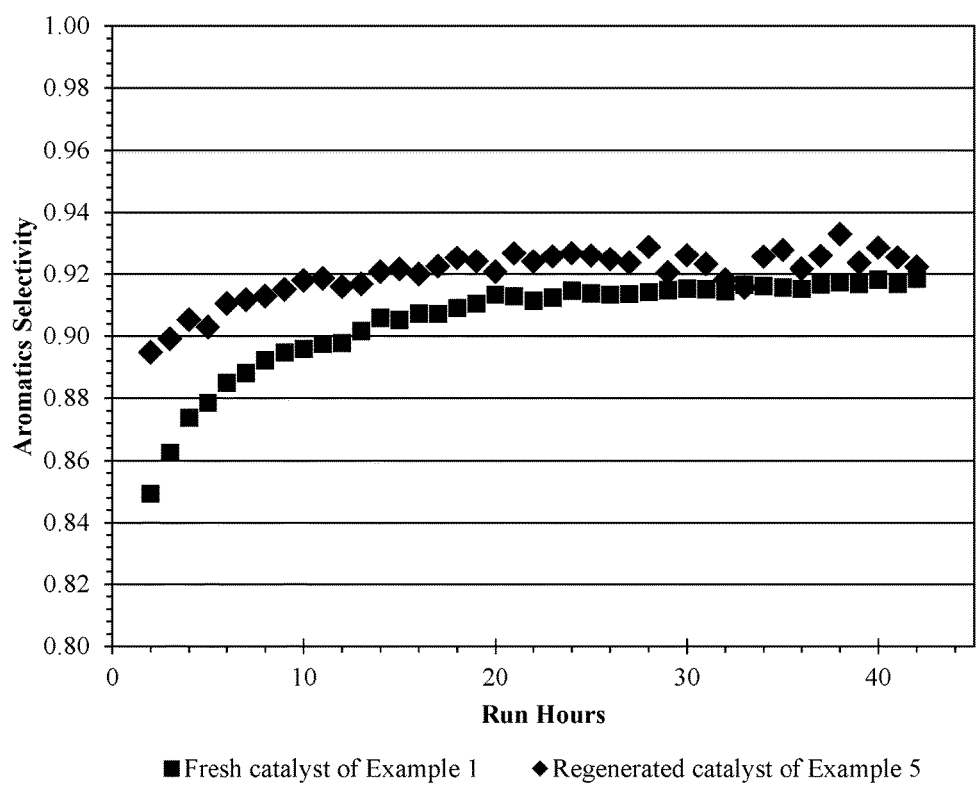
FIG. 7 presents a plot of the aromatics selectivity versus reaction time for the fresh catalyst of Example 1 and the regenerated catalyst of Example 5, in which the sulfur-contaminated catalyst was subjected to a KCl washing step and a halogenation step.
Figure 8:
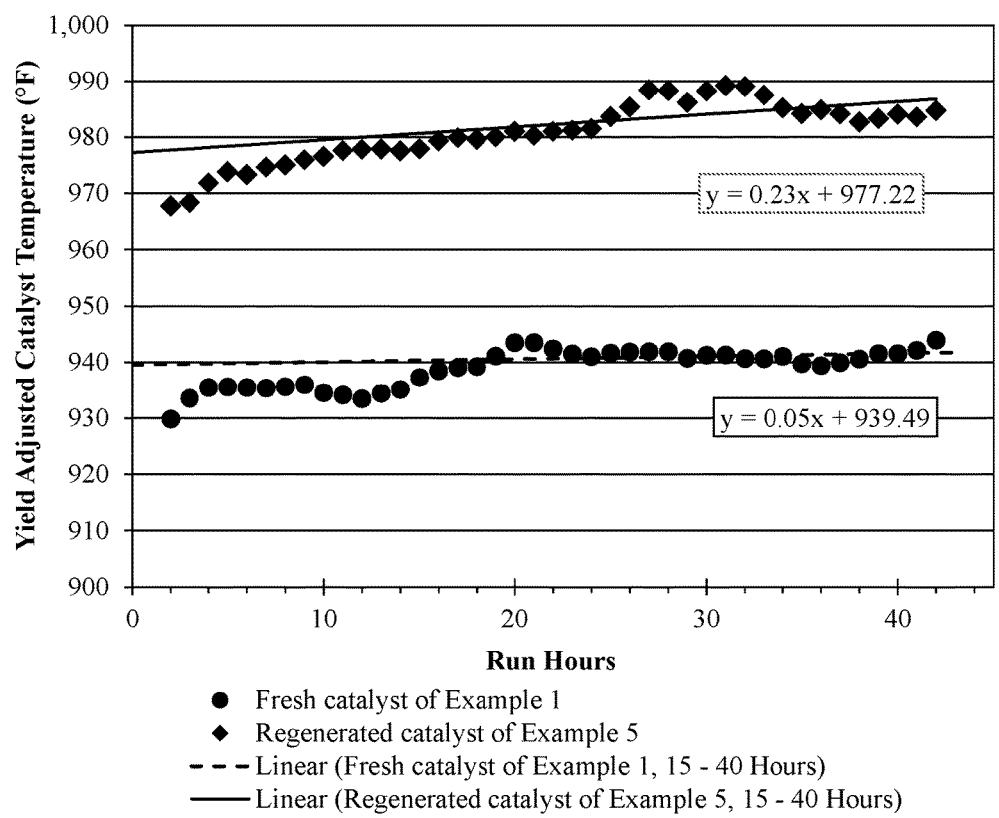
FIG. 8 presents a plot of the yield adjusted temperature versus reaction time for the fresh catalyst of Example 1 and the regenerated catalyst of Example 5, in which the sulfur-contaminated catalyst was subjected to a KCl washing step and a halogenation step.

FIG. 1 and FIG. 2, respectively, compare the aromatics selectivity and yield adjusted temperature versus the reaction time for the catalysts of Example 1 (fresh) and Example 2 (sulfur-contaminated). FIG. 3 and FIG. 4, respectively, compare the aromatics selectivity and yield adjusted temperature versus the reaction time for the catalysts of Example 1 (fresh) and Example 3 (treatment of sulfur-contaminated catalyst without washing step). FIG. 5 and FIG. 6, respectively, compare the aromatics selectivity and yield adjusted temperature versus the reaction time for the catalysts of Example 1 (fresh) and Example 4 (regeneration of sulfur-contaminated catalyst with water washing step and halogenation step). FIG. 7 and FIG. 8, respectively, compare the aromatics selectivity and yield adjusted temperature versus the reaction time for the catalysts of Example 1 (fresh) and Example 5 (regeneration of sulfur-contaminated catalyst with KCl washing step and halogenation step). Table I summarizes certain properties of the catalysts of Examples 1-5 and relevant performance metrics from FIGS. 1-8.

As shown in the table and figures, the sulfur-contaminated catalyst of Example 2 contained 178 ppmw of elemental S and was almost completely deactivated: the aromatics yield at 1000° F. was only 6%, the aromatics selectivity was approximately 20%, and a temperature of over 1100° F. was needed to achieve 63% aromatics yield. As compared to the sulfur-contaminated catalyst, some activity and selectivity were recovered using the treatment procedure of Example 3; however, no sulfur was removed from the catalyst, leading to an unacceptably high TSOR, TEOR, and fouling rate, and very low aromatics selectivity.

The regeneration procedure of Example 4 included a water wash step and a halogenation step, and the regenerated catalyst of Example 4, unexpectedly, had excellent activity (low TSOR and TEOR), a low fouling rate, and an aromatics selectivity approaching that of the fresh catalyst (Example 1). The regeneration procedure of Example 5 included a KCl wash step and a halogenation step, and the regenerated catalyst of Example 5, unexpectedly, had the best performance of all the treated/regenerated catalysts: lowest TSOR, lowest TEOR, lowest fouling rate, and highest aromatics selectivity (notably, with an aromatics selectivity equivalent to or better than that of the fresh catalyst of Example 1). Moreover, this was achieved despite the catalyst of Example 5 having the lowest surface area and micropore volume. Additionally, although a large portion (~40%) of the sulfur was removed, there was still a significant amount of sulfur remaining on the regenerated catalyst of Example 5.

TABLE I

Examples 1-5.

| Example | Catalyst | Platinum Dispersion (%) | Surface Area (m²/g) | Micropore Volume (cc/g) | Sulfur (ppmw) | Aromatics Yield at 1000° F. | TSOR (° F.) | TEOR (° F.) | Fouling Rate (° F./hr) |
|---|---|---|---|---|---|---|---|---|---|
| 1 | Fresh | 67 | 178 | 0.062 | N/A | >63% | 939 | 942 | 0.05 |
| 2 | Sulfur-Contaminated | 27 | 147 | 0.047 | 178 | 6% | 1107 | N/A | N/A |
| 3 | Halogenation Only | 33 | 110 | 0.030 | 190 | 63% | 995 | 1024 | 0.72 |
| 4 | Water Wash + Halogenation | — | — | — | — | >63% | 983 | 996 | 0.34 |
| 5 | KCl Wash + Halogenation | 35 | 100 | 0.026 | 107 | >63% | 977 | 985 | 0.23 |

The invention is described above with reference to numerous aspects and specific examples. Many variations will suggest themselves to those skilled in the art in light of the above detailed description. All such obvious variations are within the full intended scope of the appended claims. Other aspects of the invention may include, but are not limited to, the following (aspects are described as "comprising" but, alternatively, may "consist essentially of" or "consist of"):

Aspect 1. A reforming method comprising:

(A) contacting a hydrocarbon feed with an aromatization catalyst comprising a transition metal and a catalyst support under reforming conditions in a reactor system to produce an aromatic product;

(B) contacting a sulfur-contaminated hydrocarbon feed with the aromatization catalyst for a time period sufficient to form a sulfur-contaminated catalyst;

(C) washing the sulfur-contaminated catalyst with an aqueous solution to produce a washed catalyst, the aqueous solution optionally comprising an alkali metal; and (D) contacting the washed catalyst with a halogen solution comprising chlorine, fluorine, or mixtures thereof, to produce a halogenated catalyst.

Aspect 2. The method defined in aspect 1, wherein the reforming method is an in situ process, for example, steps (A)-(D) are performed in the same reactor system.

Aspect 3. The method defined in aspect 1, wherein step (C), step (D), or both steps (C) and (D), is/are performed externally to the reactor system of steps (A)-(B), for example, step (C), step (D), or both steps (C) and (D) is/are performed in a vessel that is not in the reforming reactor system.

Aspect 4. The method defined in any one of aspects 1-3, further comprising a step of reactivating the halogenated catalyst after step (D) to form a reactivated catalyst.

Aspect 5. A method of regenerating a sulfur-contaminated catalyst comprising a transition metal and a catalyst support, the method comprising:

(1) washing the sulfur-contaminated catalyst with an aqueous solution, the aqueous solution optionally comprising an alkali metal, to produce a washed catalyst; and (2) contacting the washed catalyst with a halogen solution comprising chlorine, fluorine, or mixtures thereof, to produce a halogenated catalyst.

Aspect 6. The method defined in any one of the preceding aspects, wherein the aqueous solution comprises an alkali metal, for example, sodium, potassium, rubidium, cesium, or combinations thereof.

Aspect 7. The method defined in any one of the preceding aspects, wherein the aqueous solution comprises an alkali metal salt.

Aspect 8. The method defined in any one of the preceding aspects, wherein the aqueous solution comprises an alkali metal chloride salt.

Aspect 9. The method defined in any one of aspects 1-8, wherein the alkali metal comprises potassium.

Aspect 10. The method defined in any one of aspects 1-8, wherein the alkali metal comprises rubidium.

Aspect 11. The method defined in any one of aspects 1-8, wherein the alkali metal comprises cesium.

Aspect 12. The method defined in any one of the preceding aspects, wherein the washing step (step (C), step (1)) comprises contacting the sulfur-contaminated catalyst with any aqueous solution disclosed herein, for example, consisting essentially of or consisting of water, an alkali metal salt and water, or an alkali metal salt and deionized water.

Aspect 13. The method defined in any one of the preceding aspects, wherein the washing step is conducted at any washing temperature disclosed herein, for example, in a range from about 20° C. to about 95° C., from about 15° C. to about 65° C., or from about 30° C. to about 50° C.

Aspect 14. The method defined in any one of the preceding aspects, wherein the washing step includes any number of washing cycles (for example, from 1 to 4, or from 2 to 8) and any washing cycle time periods disclosed herein (for example, in a range of from about 1 min to about 6 hr, or from about 5 min to about 2 hr).

Aspect 15. The method defined in any one of the preceding aspects, wherein the concentration of the alkali metal in the aqueous solution is in any concentration range disclosed herein, for example, from about 0.01 M to about 5 M, from about 0.01 M to about 1 M, from about 0.1 M to about 1 M, or from about 0.05 M to about 0.5 M.

Aspect 16. The method defined in any one of the preceding aspects, wherein the ratio of the weight of the aqueous solution to the weight of the sulfur-contaminated catalyst is in any range of weight ratios disclosed herein, for example, from about 0.4:1 to about 10:1, from about 0.5:1 to about 8:1, or from about 1:1 to about 5:1.

Aspect 17. The method defined in any one of the preceding aspects, wherein the washing step enriches the sulfur-contaminated catalyst with any molar amount of alkali metal disclosed herein, for example, from about 0.05 moles to about 1 mole, from about 0.1 moles to about 0.9 moles, or from about 0.05 moles to about 0.7 moles, of alkali metal per kg of the sulfur-contaminated catalyst (or per kg of the washed catalyst).

Aspect 18. The method defined in any one of the preceding aspects, wherein the washed catalyst comprises any weight percentage of sodium disclosed herein, for example, from 0 wt. % to about 0.35 wt. %, from 0 wt. % to about 0.3 wt. %, from about 0.03 wt. % to about 0.35 wt. %, or from about 0.05 wt. % to about 0.3 wt. % sodium, based on the weight of the washed catalyst.

Aspect 19. The method defined in any one of the preceding aspects, wherein the sulfur-contaminated catalyst comprises any amount of sulfur disclosed herein, for example, at least about 100 ppm, at least about 150 ppmw, from about 100 ppmw to about 1000 ppmw, from about 100 ppmw to about 500 ppmw, or from about 125 ppmw to about 1250 ppmw sulfur, based on the weight of the sulfur-contaminated catalyst.

Aspect 20. The method defined in any one of the preceding aspects, wherein the method reduces the amount of sulfur (in ppmw) by any amount disclosed herein, for example, by at least about 20%, by at least about 35%, or by from about 25% to about 95%, based on difference in the amount of sulfur (in ppmw) in the washed catalyst (or the halogenated catalyst) and the sulfur-contaminated catalyst.

Aspect 21. The method defined in any one of the preceding aspects, wherein the halogen solution comprises (or consists essentially of, or consists of) a chlorine-containing compound, a fluorine-containing compound, or mixtures thereof, and any solvent disclosed herein, for example, water or a hydrocarbon solvent.

Aspect 22. The method defined in aspect 21, wherein the chlorine-containing compound comprises hydrochloric acid, carbon tetrachloride, tetrachloroethylene, chlorobenzene, methyl chloride, methylene chloride, chloroform, allyl chloride, trichloroethylene, a chloramine, a chlorine oxide, a chlorine acid, chlorine dioxide, dichlorine monoxide, dichlorine heptoxide, chloric acid, perchloric acid, ammonium chloride, tetramethylammonium chloride, tetraethylammonium chloride, tetrapropylammonium chloride, tetrabutylammonium chloride, methyltriethylammonium chloride, or any combination thereof.

Aspect 23. The method defined in aspect 21, wherein the chlorine-containing compound comprises hydrochloric acid, ammonium chloride, tetramethylammonium chloride, or a combination thereof.

Aspect 24. The method defined in any one of aspects 21-23, wherein the fluorine-containing compound comprises hydrofluoric acid, 2,2,2-trifluoroethanol, tetrafluoroethylene, carbon tetrafluoride, carbon trifluoride, fluoromethane, heptafluoropropane, decafluorobutane, hexafluoroisopropanol, tetrafluoropropanol, pentafluoropropanol, hexafluorophenylpropanol, perfluorobutyl alcohol, hexafluor-2-propanol, pentafluoro-1-propanol, tetrafluoro-1-propanol, 1,1,1,3,3,3-hexafluoro-2-propanol, 2,2,3,3,3-pentafluoro-1-propanol, ammonium fluoride, tetramethylammonium fluoride, tetraethylammonium fluoride, tetrapropylammonium fluoride, tetrabutylammonium fluoride, methyltriethylammonium fluoride, or any combination thereof.

Aspect 25. The method defined in any one of aspects 21-24, wherein the fluorine-containing compound comprises hydrofluoric acid, ammonium fluoride, tetramethylammonium fluoride, or a combination thereof.

Aspect 26. The method defined in any one of aspects 21-25, wherein the halogen solution comprises (or consists essentially of, or consists of) the chlorine-containing compound (for example, ammonium chloride), the fluorine-containing compound (for example, ammonium fluoride), and water.

Aspect 27. The method defined in any one of aspects 1-20, wherein the halogen solution comprises (or consists essentially of, or consists of) a chlorine/fluorine-containing compound (or chlorofluorocarbon), and any solvent disclosed herein, for example, water or a hydrocarbon solvent.

Aspect 28. The method defined in any one of the preceding aspects, wherein the halogen solution comprises a concentration of chlorine (Cl) in any range disclosed herein, for example, from about 0.01 wt. % to about 10 wt. %, from about 0.1 wt. % to about 10 wt. %, or from about 0.5 wt. % to about 5 wt. %.

Aspect 29. The method defined in any one of the preceding aspects, wherein the halogen solution comprises a concentration of fluorine (F) in any range disclosed herein, for example, from about 0.01 wt. % to about 10 wt. %, from about 0.1 wt. % to about 10 wt. %, or from about 0.5 wt. % to about 5 wt. %.

Aspect 30. The method defined in any one of the preceding aspects, wherein the halogenation step (step (D), step (2)) is conducted at a halogenation temperature in any halogenation temperature range disclosed herein, for example, from about 0° C. to about 80° C., from about 5° C. to about 50° C., or from about 15° C. to about 35° C.

Aspect 31. The method defined in any one of the preceding aspects, wherein the halogenation step is conducted for a time period in any range of halogenation time periods disclosed herein, for example, from about 1 min to about 48 hr, from about 30 min to about 12 hr, or from about 1 hr to about 10 hr.

Aspect 32. The method defined in any one of the preceding aspects, wherein the method further comprises a drying step after the halogenation step, the drying step comprising subjecting the halogenated catalyst to conditions sufficient to reduce the solvent content of the halogenated catalyst to less than any residual solvent content disclosed herein, for example, less than about 15 wt. %, less than about 10 wt. %, or less than about 8 wt. % solvent.

Aspect 33. The method defined in aspect 32, wherein the conditions sufficient to reduce the solvent content comprise any suitable drying time, drying temperature, and drying pressure.

Aspect 34. The method defined in aspect 32, wherein the conditions sufficient to reduce the solvent content comprise a drying time in a range from about 1 hr to about 48 hr, or from about 2 hr to about 24 hr, a drying temperature in a range from about 15° C. to about 200° C., or from about 25° C. to about 150° C., and a drying pressure equal to atmospheric pressure or equal to any suitable sub-atmospheric pressure.

Aspect 35. The method defined in any one of the preceding aspects, wherein the method further comprises a calcination step after the halogenation step, the calcination step comprising subjecting the halogenated catalyst to any suitable calcination conditions.

Aspect 36. The method defined in aspect 35, wherein the calcination step is conducted at calcination conditions comprising a calcination temperature in any calcination temperature range disclosed herein, for example, from about 200° C. to about 800° C., from about 250° C. to about 500° C., or from about 250° C. to about 350° C.

Aspect 37. The method defined in any one of aspects 35-36, wherein the calcination step is conducted at calcination conditions comprising a calcination time in any range of calcination time periods disclosed herein, for example, from about 15 min to about 48 hr, from about 15 min to about 12 hr, or from about 30 min to about 8 hr.

Aspect 38. The method defined in any one of the preceding aspects, wherein the method further comprises a reducing step after the halogenation step, the reducing step comprising contacting the halogenated catalyst with a reducing gas stream comprising (or consisting essentially of, or consisting of) molecular hydrogen.

Aspect 39. The method defined in aspect 38, wherein the reducing gas stream comprises a mole % of molecular hydrogen greater than any minimum amount or in any range disclosed herein, for example, greater than about 25 mole %, or greater than about 75 mole %.

Aspect 40. The method defined in any one of aspects 38-39, wherein the reducing step is conducted at a peak reducing temperature in any peak reducing temperature range disclosed herein, for example, from about 200° C. to about 600° C., or from about 400° C. to about 600° C.

Aspect 41. The method defined in any one of aspects 38-40, wherein the reducing step is conducted for a time period in any range of reducing step time periods disclosed herein, for example, from about 10 hr to about 30 hr.

Aspect 42. The method defined in any one of the preceding aspects, wherein the method further comprises a carbon burn step before the washing step, after the washing step, or before and after the washing step, the carbon burn step comprising contacting the sulfur-contaminated catalyst (or the washed catalyst) with a decoking gas stream comprising oxygen.

Aspect 43. The method defined in aspect 42, wherein the decoking gas stream comprises (or consists essentially of, or consists of) any combination of an inert gas (one or more) and oxygen disclosed herein, for example, a mixture of nitrogen and oxygen, air, or a mixture of air and nitrogen.

Aspect 44. The method defined in any one of aspects 42-43, wherein the decoking gas stream comprises a mole % of oxygen less than any maximum amount or in any range disclosed herein, for example, less than about 5 mole %, or in a range from about 0.5 mole % to about 3 mole %.

Aspect 45. The method defined in any one of aspects 42-44, wherein the decoking gas stream is substantially free of halogen-containing compounds (substantially halogen-free, substantially chlorine-free), for example, less than 100 ppmw.

Aspect 46. The method defined in any one of aspects 42-45, wherein the decoking gas stream is substantially free of water, for example, less than 100 ppmw.

Aspect 47. The method defined in any one of aspects 42-46, wherein the carbon burn step is conducted at a peak decoking temperature in any peak decoking temperature range disclosed herein, for example, from about 150° C. to about 600° C., from about 200° C. to about 500° C., or from about 350° C. to about 450° C.

Aspect 48. The method defined in any one of aspects 42-47, wherein the carbon burn step is conducted for a time period in any range of de-coking time periods disclosed herein, for example, from about 1 hr to about 72 hr, from about 12 hr to about 48 hr, or from about 1 hr to about 6 hr.

Aspect 49. The method defined in any one of aspects 42-48, wherein the carbon burn step is conducted for a time period sufficient to reduce the wt. % of carbon on the catalyst to less than any maximum weight percentage of carbon disclosed herein, for example, less than about 5 wt. %, or less than about 1 wt. %.

Aspect 50. The method defined in any one of the preceding aspects, wherein the method further comprises a hydrocarbon removal step prior to the washing step, the hydrocarbon removal step comprising contacting the sulfur-contaminated catalyst with a hydrocarbon removal gas stream comprising oxygen.

Aspect 51. The method defined in aspect 50, wherein the hydrocarbon removal gas stream comprises (or consists essentially of, or consists of) any combination of an inert gas (one or more) and oxygen disclosed herein, for example, a mixture of nitrogen and oxygen, or air.

Aspect 52. The method defined in any one of aspects 50-51, wherein the hydrocarbon removal gas stream comprises a mole % of oxygen less than any maximum amount or in any range disclosed herein, for example, less than about 5 mole %, or in a range from about 0.5 mole % to about 3 mole %.

Aspect 53. The method defined in any one of aspects 50-52, wherein the hydrocarbon removal gas stream is substantially free of halogen-containing compounds (substantially halogen-free), for example, less than 100 ppmw.

Aspect 54. The method defined in any one of aspects 50-53, wherein the hydrocarbon removal gas stream is substantially free of water, for example, less than 100 ppmw.

Aspect 55. The method defined in any one of aspects 50-54, wherein the hydrocarbon removal step is conducted at a hydrocarbon removal temperature in any hydrocarbon removal temperature range disclosed herein, for example, from about 150° C. to about 250° C.

Aspect 56. The method defined in any one of aspects 50-55, wherein the hydrocarbon removal step is conducted for a time period in any range of hydrocarbon removal time periods disclosed herein, for example, from about 2 hr to about 24 hr.

Aspect 57. The method defined in any one of aspects 50-56, wherein the hydrocarbon removal step is conducted for a time period sufficient to reduce the wt. % of hydrocarbons on the sulfur-contaminated catalyst to any range of weight percentages of hydrocarbons disclosed herein, for example, from about 1 wt. % to 10 wt. %, or from about 1 wt. % to about 5 wt. %.

Aspect 58. The method defined in any one of the preceding aspects, wherein the catalyst support comprises a zeolite, an amorphous inorganic oxide, or any combination thereof.

Aspect 59. The method defined in any one of the preceding aspects, wherein the catalyst support comprises an L-zeolite, a Y-zeolite, a mordenite, an omega zeolite, a beta zeolite, or mixtures thereof.

Aspect 60. The method defined in any one of the preceding aspects, wherein the catalyst support comprises a potassium L-zeolite or a barium ion-exchanged L-zeolite.

Aspect 61. The method defined in any one of the preceding aspects, wherein the catalyst comprises a support matrix comprising alumina, silica, a mixed oxide thereof, or a mixture thereof.

Aspect 62. The method defined in any one of the preceding aspects, wherein the transition metal comprises a Group 10-11 transition metal.

Aspect 63. The method defined in any one of the preceding aspects, wherein the transition metal comprises platinum.

Aspect 64. The method defined in any one of the preceding aspects, wherein the sulfur-contaminated catalyst further comprises chlorine at any weight percentage disclosed herein, for example, from greater than 0 wt. % to about 5 wt. % chlorine, from about 0.05 wt. % to about 2 wt. % chlorine, or from about 0.1 wt. % to about 1 wt. % chlorine.

Aspect 65. The method defined in any one of the preceding aspects, wherein the sulfur-contaminated catalyst further comprises fluorine at any weight percentage disclosed herein, for example, from greater than 0 wt. % to about 5 wt. % fluorine, from about 0.05 wt. % to about 2 wt. % fluorine, or from about 0.1 wt. % to about 1 wt. % fluorine.

Aspect 66. The method defined in any one of the preceding aspects, wherein the sulfur-contaminated catalyst contains less than about 0.1 wt. % of barium, for example, less than about 0.01 wt. % barium, or no barium (no measurable amount).

Aspect 67. A reactivated catalyst or a regenerated catalyst (e.g., a halogenated catalyst) produced by the method defined in any one of the preceding aspects.

Aspect 68. The reactivated catalyst or regenerated catalyst defined in aspect 67, wherein the reactivated catalyst or regenerated catalyst comprises any amount of the alkali metal disclosed herein, for example, from about 0.5 wt. % to about 15 wt. %, from about 1 wt. % to about 14 wt. %, or from about 2 wt. % to about 13 wt. % alkali metal.

Aspect 69. The reactivated catalyst or regenerated catalyst defined in aspect 67 or 68, wherein the reactivated catalyst or regenerated catalyst comprises any amount of sulfur disclosed herein, for example, less than about 400 ppmw, less than about 200 ppmw, less than about 150 ppmw, from about 25 ppmw to about 400 ppmw, from about 70 ppmw to about 200 ppmw, or from about 50 ppmw to about 150 ppmw sulfur.

Aspect 70. The reactivated catalyst or regenerated catalyst defined in any one of aspects 67-69, wherein the reactivated catalyst or regenerated catalyst comprises any amount of carbon disclosed herein, for example, from about 0.01 wt. % to about 5 wt. %, from about 0.1 wt. % to about 1 wt. %, or from about 0.25 wt. % to about 0.5 wt. % carbon.

Aspect 71. The reactivated catalyst or regenerated catalyst defined in any one of aspects 67-70, wherein the reactivated catalyst or regenerated catalyst comprises any amount of chlorine disclosed herein, for example, from about 0.01 wt. % to about 10 wt. %, from about 0.1 wt. % to about 10 wt. %, or from about 0.5 wt. % to about 5 wt. % chlorine.

Aspect 72. The reactivated catalyst or regenerated catalyst defined in any one of aspects 67-71, wherein the reactivated catalyst or regenerated catalyst comprises any amount of fluorine disclosed herein, for example, from about 0.01 wt. % to about 10 wt. %, from about 0.1 wt. % to about 10 wt. %, or from about 0.5 wt. % to about 5 wt. % fluorine.

Aspect 73. The reactivated catalyst or regenerated catalyst defined in any one of aspects 67-72, wherein the surface area of the reactivated catalyst or regenerated catalyst is at least about 40%, at least about 50%, or at least about 60% of the surface area of the sulfur-contaminated catalyst.

Aspect 74. The reactivated catalyst or regenerated catalyst defined in any one of aspects 67-73, wherein the reactivated catalyst or regenerated catalyst is characterized by a TEOR within about 70° F., within about 60° F., within about 55° F., or within about 50° F., of the TEOR of a fresh reference catalyst.

Aspect 75. The reactivated catalyst or regenerated catalyst defined in any one of aspects 67-74, wherein the reactivated catalyst or regenerated catalyst is characterized by a TSOR within about 55° F., within about 50° F., within about 45° F., or within about 40° F., of the TSOR of a fresh reference catalyst.

Aspect 76. The reactivated catalyst or regenerated catalyst defined in any one of aspects 67-75, wherein the reactivated catalyst or regenerated catalyst is characterized by a fouling rate (FR) in any range disclosed herein, for example, from about 0.05° F./hr to about 0.6° F./hr, from about 0.05° F./hr to about 0.5° F./hr, from about 0.1° F./hr to about 0.5° F./hr, or from about 0.15° F./hr to about 0.45° F./hr.

Aspect 77. The reactivated catalyst or regenerated catalyst defined in any one of aspects 67-76, wherein the reactivated catalyst or regenerated catalyst is characterized by an aromatics selectivity in any selectivity range disclosed herein, for example, from about 0.88 to about 0.94, or from about 0.89 to about 0.94.

Aspect 78. The reactivated catalyst or regenerated catalyst defined in any one of aspects 67-77, wherein the reactivated catalyst or regenerated catalyst is characterized by a platinum dispersion in any platinum dispersion range disclosed herein, for example, from about 20% to about 50%, or from about 25% to about 55%.

Aspect 79. The method or catalyst defined in any one of the preceding aspects, wherein the catalyst (aromatization catalyst, sulfur-contaminated catalyst, regenerated catalyst (e.g., halogenated catalyst), reactivated catalyst) comprises any weight percentage of transition metal disclosed herein, for example, from about 0.1 wt. % to about 10 wt. %, or from about 0.3 wt. % to about 5 wt. %, transition metal.

Aspect 80. The method or catalyst defined in any one of the preceding aspects, wherein the catalyst (aromatization catalyst, sulfur-contaminated catalyst, regenerated catalyst (e.g., halogenated catalyst), reactivated catalyst) comprises any weight percentage of platinum disclosed herein, for example, from about 0.1 wt. % to about 10 wt. %, or from about 0.5 wt. % to about 2 wt. %, platinum.

Aspect 81. The method or catalyst defined in any one of the preceding aspects, wherein the catalyst (aromatization catalyst, sulfur-contaminated catalyst, regenerated catalyst (e.g., halogenated catalyst), reactivated catalyst) comprises platinum and a zeolitic support comprising a KL-zeolite.

I claim:

1. A method for regenerating a sulfur-contaminated catalyst comprising a transition metal and a catalyst support, the method comprising:
   (1) washing the sulfur-contaminated catalyst with an aqueous solution, the aqueous solution optionally comprising an alkali metal, to produce a washed catalyst; and
   (2) contacting the washed catalyst with a halogen solution comprising chlorine and fluorine to produce a halogenated catalyst.

2. The method of claim 1, wherein the aqueous solution comprises the alkali metal.

3. The method of claim 2, wherein:
   the transition metal comprises platinum;
   the catalyst support comprises a KL-zeolite and a support matrix comprising alumina, silica, a mixed oxide thereof, or a mixture thereof; and
   the sulfur-contaminated catalyst comprises:
      from about 100 ppmw to about 1000 ppmw sulfur;
      from about 0.05 wt. % to about 2 wt. % chlorine; and
      from about 0.05 wt. % to about 2 wt. % fluorine.

4. The method of claim 3, wherein the sulfur-contaminated catalyst contains less than about 0.1 wt. % of barium.

5. The method of claim 1, wherein the aqueous solution comprises a salt of potassium, rubidium, cesium, or any combination thereof.

6. The method of claim 1, wherein:
   step (1) comprises from 2 to 8 washing cycles;
   each washing cycle is conducted independently at a washing temperature in a range from about 20° C. to about 95° C. and for a time period in a range from about 5 minutes to about 2 hours; and
   each washing cycle is conducted independently with either an aqueous solution comprising the alkali metal or an aqueous solution that does not contain an alkali metal.

7. The method of claim 6, wherein a ratio of the weight of the aqueous solution to the weight of the sulfur-contaminated catalyst in each washing cycle independently is in a range from about 0.4:1 to about 10:1.

8. The method of claim 1, wherein the halogen solution comprises a chlorine-containing compound, a fluorine-containing compound, and water.

9. The method of claim 1, wherein the halogen solution comprises:
from about 0.01 wt. % to about 10 wt. % chlorine; and
from about 0.01 wt. % to about 10 wt. % fluorine.

10. The method of claim 1, wherein the halogenated catalyst comprises:
from about 0.5 wt. % to about 2 wt. % platinum;
a catalyst support comprising a KL-zeolite and a support matrix comprising alumina, silica, a mixed oxide thereof, or a mixture thereof;
from about 0.5 wt. % to about 5 wt. % chlorine; and
from about 0.5 wt. % to about 5 wt. % fluorine.

11. The method of claim 10, wherein the halogenated catalyst contains less than about 0.1 wt. % of barium.

12. The method of claim 1, wherein the method removes at least about 25% of the sulfur from the sulfur-contaminated catalyst, based on the difference in the ppmw of sulfur in the halogenated catalyst and the sulfur-contaminated catalyst.

13. The method of claim 1, further comprising a drying step after step (2), a calcination step after step (2), or both a drying step and a calcination step after step (2).

14. The method of claim 1, further comprising a carbon burn step before step (1), after step (1), or both before and after step (1).

15. The method of claim 1, wherein the halogenated catalyst is characterized by:
a TEOR (end of run temperature) within about 70° F. of the TEOR of a fresh reference catalyst;
a FR (fouling rate) in a range from about 0.05° F./hr to about 0.6° F./hr; and
an aromatics selectivity in a range from about 0.88 to about 0.94.

16. The method of claim 1, further comprising a reducing step after the halogenation step, the reducing step comprising contacting the halogenated catalyst with a reducing gas stream comprising molecular hydrogen to produce a reactivated catalyst.

17. The method of claim 16, wherein the reactivated catalyst is characterized by:
a TEOR (end of run temperature) within about 55° F. of the TEOR of a fresh reference catalyst;
a FR (fouling rate) in a range from about 0.1° F./hr to about 0.5° F./hr; and
an aromatics selectivity in a range from about 0.89 to about 0.94.

18. A reforming method comprising:
(A) contacting a hydrocarbon feed with an aromatization catalyst comprising a transition metal and a catalyst support under reforming conditions in a reactor system to produce an aromatic product;
(B) contacting a sulfur-contaminated hydrocarbon feed with the aromatization catalyst for a time period sufficient to form a sulfur-contaminated catalyst;
(C) washing the sulfur-contaminated catalyst with an aqueous solution to produce a washed catalyst, the aqueous solution optionally comprising an alkali metal; and
(D) contacting the washed catalyst with a halogen solution comprising chlorine and fluorine to produce a halogenated catalyst.

19. The method of claim 18, wherein the reforming method is an in situ process.

20. The method of claim 18, wherein at least one of steps (C) and (D) is performed in a vessel external to the reactor system.

21. The method of claim 18, wherein:
the transition metal comprises platinum;
the catalyst support comprises a KL-zeolite and a support matrix comprising alumina, silica, a mixed oxide thereof, or a mixture thereof; and
the sulfur-contaminated catalyst comprises:
from about 100 ppmw to about 1000 ppmw sulfur;
from greater than 0 wt. % to about 5 wt. % chlorine; and
from greater than 0 wt. % to about 5 wt. % fluorine.

22. The method of claim 21, wherein the sulfur-contaminated catalyst contains less than about 0.1 wt. % of barium.

23. The method of claim 21, wherein the aqueous solution comprises a salt of potassium, rubidium, cesium, or any combination thereof.

24. The method of claim 18, wherein the halogenated catalyst comprises:
from about 0.5 wt. % to about 2 wt. % platinum;
a catalyst support comprising a KL-zeolite and a support matrix comprising alumina, silica, a mixed oxide thereof, or a mixture thereof;
from about 0.5 wt. % to about 5 wt. % chlorine; and
from about 0.5 wt. % to about 5 wt. % fluorine.

25. A method for regenerating a sulfur-contaminated catalyst comprising a transition metal and a catalyst support, the method comprising:
(1) washing the sulfur-contaminated catalyst with an aqueous solution, the aqueous solution optionally comprising an alkali metal, to produce a washed catalyst;
(2) contacting the washed catalyst with a halogen solution comprising chlorine and fluorine to produce a halogenated catalyst; and
(3) drying and calcining the halogenated catalyst to produce a regenerated catalyst.

26. The method of claim 25, wherein:
the transition metal comprises platinum; and
the catalyst support comprises a KL-zeolite and a support matrix comprising alumina, silica, a mixed oxide thereof, or a mixture thereof.

27. The method of claim 26, wherein the aqueous solution comprises potassium.

28. The method of claim 26, wherein the halogen solution comprises a chlorine-containing compound, a fluorine-containing compound, and water.

29. The method of claim 26, wherein the method removes from about 25% to about 95% of the sulfur from the sulfur-contaminated catalyst, based on the difference in the ppmw of sulfur in the regenerated catalyst and the sulfur-contaminated catalyst.

30. The method of claim 26, wherein:
the sulfur-contaminated catalyst comprises:
at least about 100 ppmw sulfur; and
less than about 0.1 wt. % of barium; and
the regenerated catalyst comprises:
from about 0.5 wt. % to about 2 wt. % platinum;
from about 0.5 wt. % to about 5 wt. % chlorine; and
from about 0.5 wt. % to about 5 wt. % fluorine.

31. The method of claim 26, wherein:
drying comprises subjecting the halogenated catalyst to a drying temperature in a range from about 15° C. to about 200° C. at a sub-atmospheric pressure; and
calcining comprises subjecting the halogenated catalyst to a calcination temperature in a range from about 200° C. to about 800° C. for a time period in a range from about 30 minutes to about 8 hours.

32. The method of claim 26, wherein the regenerated catalyst is characterized by:
a FR (fouling rate) in a range from about 0.05° F./hr to about 0.6° F./hr; and
an aromatics selectivity in a range from about 0.88 to about 0.94.

33. The method of claim 26, further comprising a reducing step after the drying and calcining step, the reducing step comprising contacting the regenerated catalyst with a reducing gas stream comprising molecular hydrogen to produce a reactivated catalyst; wherein the reactivated catalyst is characterized by a FR (fouling rate) in a range from about 0.1° F./hr to about 0.5° F./hr, and an aromatics selectivity in a range from about 0.89 to about 0.94.

34. A method for regenerating a sulfur-contaminated catalyst comprising a transition metal and a catalyst support, the method comprising:
(a) washing the sulfur-contaminated catalyst with an aqueous solution, the aqueous solution optionally comprising an alkali metal, to produce a washed catalyst;
(b) contacting the washed catalyst with a decoking gas stream comprising oxygen to produce a decoked catalyst containing less than about 1 wt. % carbon; and
(c) contacting the decoked catalyst with a halogen solution comprising chlorine and fluorine to produce a halogenated catalyst.

35. The method of claim 34, wherein step (b) is conducted at a peak decoking temperature in a range from about 150° C. to about 600° C.

36. The method of claim 34, wherein:
the transition metal comprises platinum;
the catalyst support comprises a KL-zeolite and a support matrix comprising alumina, silica, a mixed oxide thereof, or a mixture thereof;
the sulfur-contaminated catalyst comprises:
at least about 100 ppmw sulfur; and
less than about 0.1 wt. % of barium; and
the halogenated catalyst comprises:
from about 0.1 wt. % to about 10 wt. % platinum;
from about 0.1 wt. % to about 10 wt. % chlorine; and
from about 0.1 wt. % to about 10 wt. % fluorine.

37. The method of claim 36, wherein:
the aqueous solution comprises a salt of potassium, rubidium, cesium, or any combination thereof; and
the halogen solution comprises a chlorine-containing compound, a fluorine-containing compound, and water.

38. The method of claim 36, wherein the method removes from about 25% to about 95% of the sulfur from the sulfur-contaminated catalyst, based on the difference in the ppmw of sulfur in the halogenated catalyst and the sulfur-contaminated catalyst.

39. The method of claim 36, further comprising a step of drying and calcining the halogenated catalyst to produce a regenerated catalyst.

40. The method of claim 39, further comprising a reducing step, the reducing step comprising contacting the regenerated catalyst with a reducing gas stream comprising molecular hydrogen to produce a reactivated catalyst.

* * * * *